United States Patent
Watanabe

(10) Patent No.: US 9,670,450 B2
(45) Date of Patent: Jun. 6, 2017

(54) CELL OR TISSUE CULTIVATION APPARATUS AND METHOD OF CULTIVATION

(71) Applicant: Purpose Co., Ltd., Fuji-shi (JP)

(72) Inventor: Setsuo Watanabe, Fuji (JP)

(73) Assignee: PURPOSE COMPANY LIMITED, Fuji-Shi (JP)

(*) Notice: Subject to any disclaimer, the term of this patent is extended or adjusted under 35 U.S.C. 154(b) by 247 days.

(21) Appl. No.: 14/642,824

(22) Filed: Mar. 10, 2015

(65) Prior Publication Data

US 2015/0175953 A1   Jun. 25, 2015

Related U.S. Application Data

(62) Division of application No. 12/307,986, filed as application No. PCT/JP2007/062409 on Jun. 20, 2007.

(30) Foreign Application Priority Data

Jul. 10, 2006   (JP) ................................. 2006-189733

(51) Int. Cl.
  *C12M 1/42*   (2006.01)
  *A61F 2/06*   (2013.01)
  (Continued)

(52) U.S. Cl.
  CPC ............. *C12M 35/04* (2013.01); *A61F 2/062* (2013.01); *C12M 21/08* (2013.01); *C12M 25/02* (2013.01); *C12M 41/14* (2013.01)

(58) Field of Classification Search
  CPC .................................................... C12M 35/04
  See application file for complete search history.

(56) References Cited

U.S. PATENT DOCUMENTS

| 5,217,899 A | 6/1993 | Shapiro et al. |
| 5,406,853 A | 4/1995 | Lintilhac et al. |

(Continued)

FOREIGN PATENT DOCUMENTS

| CA | 2543374 A1 | 5/2005 |
| CN | 1427888 | 7/2003 |

(Continued)

OTHER PUBLICATIONS

International Preliminary Report and Written Opinion of International Application No. PCT/JP2007/062409 dated Jan. 29, 2009.

(Continued)

*Primary Examiner* — Jonathan Hurst
(74) *Attorney, Agent, or Firm* — Polsinelli PC

(57) ABSTRACT

A cultivation apparatus and a cultivation method of a culture such as a cell or tissue. Provided are an incubator unit for accommodating a culture and a lever that penetrates through the incubator unit and can move in circular arc around a fulcrum as a center, the fulcrum being set at a wall of the incubator unit or in the vicinity thereof, then displacement is imparted to the culture by operating the lever. Bending force can be acted on the culture (cell construct) such as a cell or tissue, so that without any increase or decrease of a culture fluid in the incubator unit, namely, without any increase or decrease of pressure to the culture fluid, displacement required for cultivation can be imparted to the culture in the incubator unit. By curving, continuous compression and extension are generated in a direction of thickness from a concave portion to a convex portion of the curving.

12 Claims, 29 Drawing Sheets

(51) Int. Cl.
*C12M 1/12* (2006.01)
*C12M 3/00* (2006.01)
*C12M 1/00* (2006.01)

(56) References Cited

U.S. PATENT DOCUMENTS

| | | |
|---|---|---|
| 5,452,236 A | 9/1995 | Lintilhac et al. |
| 5,736,399 A | 4/1998 | Takezawa et al. |
| 6,242,247 B1 | 6/2001 | Rieser et al. |
| 6,387,693 B2 | 5/2002 | Rieser et al. |
| 6,432,713 B2 | 8/2002 | Takagi et al. |
| 7,541,178 B2 | 6/2009 | Takagi et al. |
| 7,547,540 B2 | 6/2009 | Takagi et al. |
| 7,585,323 B2 | 9/2009 | Masini et al. |
| 7,807,453 B2 | 10/2010 | Quinn et al. |
| 2001/0014473 A1 | 8/2001 | Rieser et al. |
| 2001/0021529 A1 | 9/2001 | Takagi |
| 2001/0043918 A1 | 11/2001 | Masini et al. |
| 2002/0037586 A1 | 3/2002 | Takagi et al. |
| 2003/0199083 A1 | 10/2003 | Vilendrer et al. |
| 2004/0077072 A1 | 4/2004 | Takagi et al. |
| 2004/0235153 A1 | 11/2004 | Takagi et al. |
| 2005/0048643 A1 | 3/2005 | Takagi et al. |
| 2005/0106716 A1 | 5/2005 | Takagi et al. |
| 2006/0129071 A1 | 6/2006 | Hauselmann et al. |
| 2006/0147486 A1 | 7/2006 | Kim et al. |

FOREIGN PATENT DOCUMENTS

| | | |
|---|---|---|
| CN | 1737106 | 2/2006 |
| CN | 1737107 | 2/2006 |
| CN | 1898375 A | 1/2007 |
| CN | 100354406 | 12/2007 |
| EP | 0112590 A2 | 7/1984 |
| EP | 0441639 A1 | 8/1991 |
| EP | 0671469 A2 | 9/1995 |
| EP | 0922093 | 6/1999 |
| EP | 1266960 | 12/2002 |
| EP | 1382670 | 1/2004 |
| EP | 1428869 | 6/2004 |
| EP | 1464696 | 10/2004 |
| JP | 05007487 A | 1/1993 |
| JP | 07298876 A | 11/1995 |
| JP | 09313166 | 12/1997 |
| JP | 10155475 A | 6/1998 |
| JP | 11504216 A | 4/1999 |
| JP | 2000513214 A | 10/2000 |
| JP | 3163533 B2 | 3/2001 |
| JP | 2001238663 | 9/2001 |
| JP | 2002315566 | 10/2002 |
| JP | 2003061642 | 3/2003 |
| JP | 2003-169663 A | 6/2003 |
| JP | 2003180331 | 7/2003 |
| JP | 2004512031 A | 4/2004 |
| JP | 2005143343 A | 6/2005 |
| JP | 2006513013 A | 4/2006 |
| WO | WO-9746665 | 12/1997 |
| WO | WO-0164848 | 9/2001 |
| WO | WO-0226116 | 4/2002 |
| WO | WO-03029398 A1 | 4/2003 |
| WO | WO-03054137 | 7/2003 |
| WO | WO-03085101 A1 | 10/2003 |
| WO | WO-2004094586 A2 | 11/2004 |
| WO | WO-2006015304 A2 | 2/2006 |
| WO | WO-2008007527 | 1/2008 |

OTHER PUBLICATIONS

Powell et al., "Mechanical Stimulation Improves Tissue-Engineered Human Skeletal Muscle", Am J Physiol Cell Physiol 283: C1557-C1565, 2002, first published Jul. 17, 2002.

Canadian Office Action issued in related Canadian Patent Application No. 2,658,235 on Jul. 27, 2010.

U.S. Office Action for U.S. Appl. No. 12/307,978 dated Jun. 20, 2011.

Engelmayer, Jr., et al., "A Novel Bioractor for the Dynamic Flexural Stimulation of Tissue Engineered Heart Valve Biomaterials", Biomaterials, vol. 24, pp. 2523-2532 (2003).

Sodian et al., "New Pulsatile Bioreactor for Fabrication of Tissue-Engineered Patches", *J. Biomed. Mater. Res. (App. Biomater)*, vol. 58, pp. 401-405 (2001).

Supplementary European Search Report issued in corresponding EP patent application No. 07767247.5, 8 pages. (Nov. 5, 2012).

Supplementary European Search Report issued in corresponding EP patent application No. 07767398.6, 8 pages. (Nov. 6, 2012).

Office Action issued in China for corresponding Chinese application No. 200780025260.2, dated Apr. 25, 2011.

Office Action issued in China for corresponding Chinese application No. 200780025260.2, dated Aug. 21, 2012.

Office Action issued in China for corresponding Chinese application No. 200780025260.2, dated Jun. 9, 2011.

Notice of Allowance issued in relevant U.S. Appl. No. 12/307,978, dated Dec. 14, 2012.

Office Action issued in Japan for corresponding Japanese application No. 2006189732, dated Dec. 18, 2012.

Office Action issued in China for corresponding Chinese application No. 200780026057.7, dated Nov. 26, 2012.

U.S. Office Action for U.S. Appl. No. 12/307,978 dated Dec. 16, 2011.

Brown, "Techniques for mechanical stimulation of cells in vitro: a review", J. Biomechanics, 200, pp. 3-14, vol. 33.

JP Office Action for Application No. 2006-189732 dated Jan. 24, 2012.

U.S. Office Action of U.S. Appl. No. 12/307,978 dated Jun. 20, 2011.

Office Action issued in U.S. Appl. No. 12/307,986 issued Feb. 1, 2012.

Office Action issued in U.S. Appl. No. 12/307,986 issued Sep. 13, 2012.

Office Action issued in U.S. Appl. No. 12/307,986 issued Jun. 3, 2014.

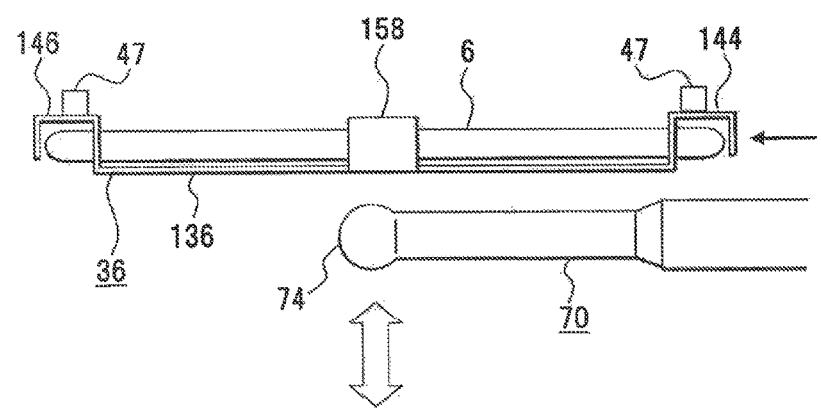
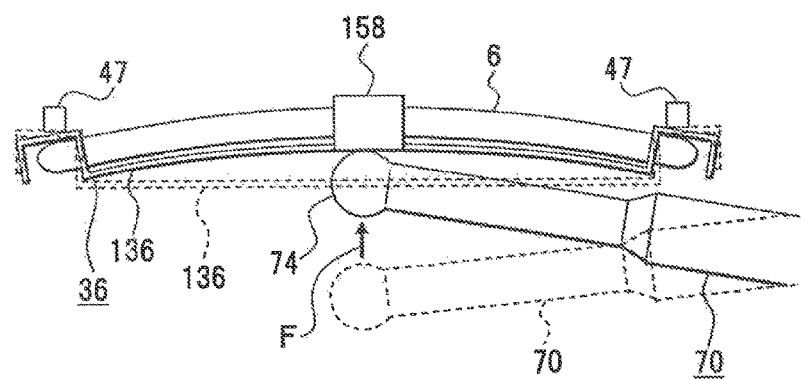

CELL OR TISSUE CULTIVATION APPARATUS AND METHOD OF CULTIVATION

CROSS-REFERENCE TO RELATED APPLICATIONS

This application is a Divisional of application Ser. No. 12/307,986, filed on Jan. 8, 2009, now U.S. Pat. No. 9,005,958, which is the National Phase of International Application No. PCT/JP2007/062409, filed on Jun. 20, 2007, and which claims priority to Japanese Patent Application Number 2006-189733, filed on Jul. 10, 2006. The entire contents of each of application is hereby incorporated herein by reference.

BACKGROUND OF THE INVENTION

1. Field of the Invention

The present invention relates to cultivation of a cell or tissue in the fields of regeneration medicine and tissue engineering, and relates to a method of three dimensional tissue cultivation for three dimensional tissue or organ regeneration. Concretely, the present invention relates to a cultivation apparatus and a cultivation method that are used in cultivation executed with one or some of a cell, a cell scaffold and an ECM (extracellular matrix) that a cell generates, as a cell construct. There may be a case where the above cultivation is executed with addition of a culture fluid, other additives, a growth factor, a chemical and so on.

In short, the cultivation apparatus and the cultivation method of the present invention differ from the conventional static cultivation. The cultivation apparatus and the cultivation method of the present invention are an apparatus relating to three dimensional cultivation where physical action is used together. The cultivation apparatus is for realizing objective regeneration tissue by promotion of differentiation or stop thereof along with growth, cell migration and substance migration that are promoted by stimulating a cell of a cell construct aggressively and displacing a cell construct.

2. Description of the Related Art

For cultivation of a cell or tissue, a method of imparting physical stimulation such as pressure and tension to a cell or tissue to be cultivated is studied, and various bioreactors and so on are suggested. Two dimension cultivation (plane cultivation) is a cultivation method using a flat bottomed culture carrier, and in general, is static cultivation in an incubator. Suspension cultivation is a method of cultivating a non-adherent cell being suspended. This method is also static cultivation in an incubator. Three dimension cultivation is a method that is generally executed such that a cell scaffold where a cell is disseminated is left still in an incubator to be cultivated. It is general for the three dimension cultivation (using a bioreactor) that a cell is made to adhere to or is enclosed by a cell scaffold to process stirring of a culture fluid and so on. It is conceived that in the three dimension cultivation of a cell scaffold, physical action such as pressure, compression, tension and shear are imparted to a cell.

A cultivation apparatus for imparting physical action is called "a bioreactor", "a tissue engineering processor", etc. Such apparatus is expected to be into practical utilization as a cell/tissue cultivation apparatus in vitro for cultivation experiments of tissue engineering and regeneration medicine.

Concerning such bioreactor having functions of cultivating a cell or tissue, and imparting physical displacement, stress and stimulation used in the cultivation, a method for cultivating a cell or tissue and an apparatus therefore are disclosed in Japanese Laid-open Patent Publication No. 2001-238663 (Abstract, etc.) as an example of using pressure and oscillation (supersonic wave), a method for in vivo, ex vivo and in vitro, repair and regeneration of cartilage and collagen, and bone remodeling is disclosed in Published Japanese Translations of PCT International Publication for Patent Application No. 2004-512031 (Abstract, etc.) as an example of using pressure, a cell and tissue-cultivating apparatus is disclosed in Japanese Laid-open Patent Publication No. 2002-315566 (Abstract, etc.) as an example of using shear force, a cell and tissue-cultivating device is disclosed in Japanese Laid-open Patent Publication No. 2003-061642 (Abstract, etc.) as an example of using tensile force, a cell and tissue cultivation apparatus is disclosed in Japanese Laid-open Patent Publication No. 2003-180331 (Abstract, etc.) as an example of using compression force, a device for cultivating cell is disclosed in Japanese Laid-open Patent Publication No. H09-313166 (Abstract, etc.) as an example of using shear force, a loading device of extending and contracting stimulation for cultivating a cell by using a silicone belt is disclosed in Japanese Laid-open Patent Publication No. H10-155475 (Abstract, etc.) as an example of using tensile force, and an apparatus executing sterilization, inoculation, cultivation, preservation, transport and test of tissue and a synthetic or natural vascular graft, and a method therefore are disclosed in Published Japanese Translations of PCT International Publication for Patent Application No. H11-504216 (Abstract, etc.) as an example of using both tension and shear. A cultivation method where distortion is given to cells held on membranes by the membranes is disclosed in Japanese Laid-open Patent Publication No. 2005-143343 (Abstract, etc.). A semi-permeable membrane being used for cultivation is disclosed in International Publication Pamphlet No. WO 2006/015304 A2 (Abstract, etc.) and Published Japanese Translations of PCT International Publication for Patent Application No. 2000-513214 A (Abstract, etc.). Imparting of various kinds of physical action and stimulation, and using of a semi-permeable membrane are tried for cultivation of a cell, etc.

There are regions receiving many kinds of stress in the human body. Tissue used for repairing these regions is different according to the regions. For example, a disc, a meniscus, a bone, fiber cartilage and a valve of a heart receive bending force in vivo. This bending stress is different from simple pressure, compression, tension, shear, etc. It is insufficient that tissue cultivated by a stimulus factor such as a simple pressure, compression, tension and shear is applied to a region receiving such bending force.

For the above, the inventors of the present invention conceive that bending is so useful for growth, etc. of a cell or tissue as stimulation or a load imparted to a cell or tissue to be cultivated. Such problem is not disclosed in the above patent documents, and is not also suggested therein.

SUMMARY OF THE INVENTION

An object of the present invention relates to a cultivation apparatus and a cultivation method for a culture including a cell and/or tissue, and is to provide an apparatus and a method for cultivating a cell and/or tissue proper for a region of a body of a human being and so on.

Another object of the present invention relates to a cultivation apparatus for a cell and/or tissue proper for a region of a body of a human being, etc., and to contribute cultivation of a proper cell and/or tissue by curving, or extending and compressing a culture.

To achieve the above object, the cultivation apparatus of the present invention can act bending force on a culture including a cell and/or tissue, so that without any increase or decrease of a culture fluid in an incubator unit, namely, without any increase or decrease of pressure on the culture fluid, displacement required for cultivation can be imparted to the culture in the incubator unit. Concretely, by curving, continuous compression and extension are generated in a direction of thickness from a concave portion to a convex portion thereof. By applying to a culture physical stimulation or a load not attained by conventional pressurization, shear and tension, a culture appropriate for restoration of tissue at a region accompanying bending is realized. The present invention is not limited to such bending, and without any increase or decrease of a culture fluid in an incubator unit, namely, without any increase or decrease of pressure on the culture fluid, motion, stimulation, etc. that are necessary for cultivation can be imparted to a culture.

To achieve the above object, a first aspect of the present invention there is provided a cultivation apparatus for a culture including a cell and/or tissue, comprising an incubator unit that accommodates the culture; and a lever that penetrates from an inside of the incubator unit to an outside thereof, wherein displacement is imparted to the culture by operating the lever. From such structure, the above objects can be achieved.

To achieve the above object, a second aspect of the present invention there is provided a cultivation apparatus for a culture including a cell and/or tissue, comprising a bed on which the culture is disposed; an incubator unit that accommodates the culture with the bed; a lever that penetrates from an inside of the incubator unit to an outside thereof; and a driving unit that pushes the bed by operating the lever, and imparts displacement to the culture by curving deformation of the bed. From such structure, the above objects can be achieved.

To achieve the above object, in the above cultivation apparatus, preferably, the lever may move in circular arc around a fulcrum as a center, the fulcrum being set at a wall of the incubator unit or in the vicinity thereof. From such structure, the above objects can be achieved.

To achieve the above object, a third aspect of the present invention there is provided a cultivation apparatus for a culture including a cell and/or tissue, comprising a bed on which the culture is disposed; an incubator unit that accommodates the culture with the bed; a lever that penetrates from an inside of the incubator unit to an outside thereof, and can move in circular arc around a fulcrum as a center, the fulcrum being set at a wall of the incubator unit or in the vicinity thereof; and a driving unit that imparts stretching force to the bed by operating the lever, and extends and contracts the culture by deformation due to extension and contraction of the bed. From such structure, the above objects can be achieved.

To achieve the above object, a fourth aspect of the present invention there is provided a cultivation method for a culture including a cell and/or tissue, comprising the steps of accommodating the culture in an incubator unit; imparting movement in circular arc around a fulcrum set at a wall of the incubator unit or in the vicinity thereof as a center, to a lever penetrating from an inside of the incubator unit to an outside thereof; and imparting bending displacement to the culture by the movement in circular arc. From such structure, the above objects can be achieved.

According to the present invention, following effects can be obtained.

(1) Displacement (stress) such as bending is applied to a culture in cultivation, and bending motion can be purely generated.

(2) It is able to be used for regeneration of tissue receiving bending force in vivo like discs, etc.

(3) It can be expected to prevent a stem cell from differentiating and prevent a tissue cell from dedifferentiating, and if tissue structure and so on have directionality, an arranging direction thereof can be uniform, and a culture equivalent to tissue in vivo can be obtained.

(4) A necessary tissue can be cultivated by bending action without other kinds of physical action such as pressure, or with the minimum thereof.

(5) Cell migration can be expected to become easy.

(6) Nutrients and oxygen can be osmosed in the interior of a three dimensional cell construct, and discharging waste products is expected.

The object and advantages of the invention will be realized and attained by means of the elements and combinations particularly pointed out in the claims. It is to be understood that both the foregoing general description and the following detailed description are exemplary and explanatory and are not restrictive of the invention, as claimed.

Other objects, features and advantages of the present invention are more clearly understood by referring to attached drawings and each of embodiments.

BRIEF DESCRIPTION OF DRAWINGS

FIG. 15A is a view showing bending motion to a cell construct;

FIG. 15B is a view showing bending motion to a cell construct;

DETAILED DESCRIPTION OF THE PREFERRED EMBODIMENTS

First Embodiment

Figure 1:
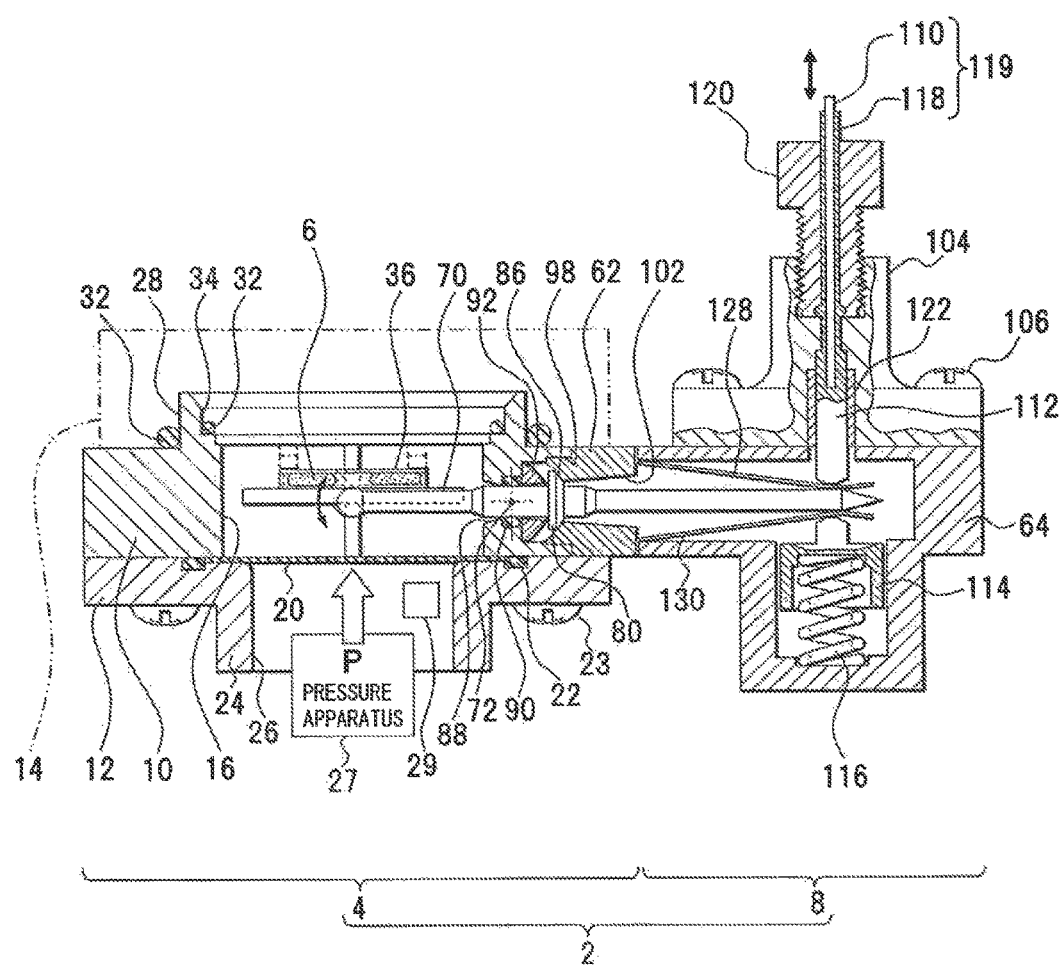
FIG. 1 is a vertical sectional view showing a culture unit of a cultivation apparatus according to a first embodiment.
Figure 2:
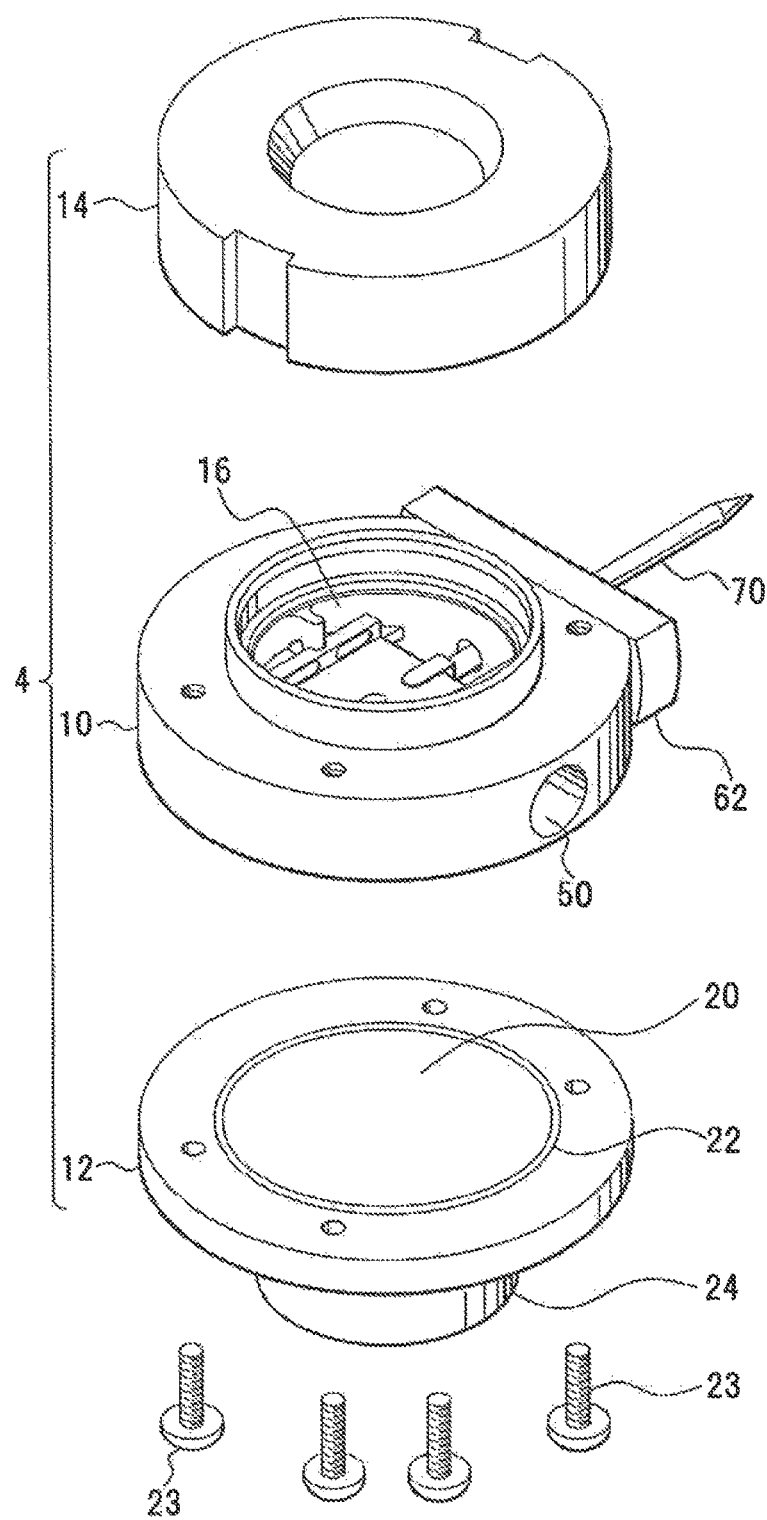
FIG. 2 is an exploded perspective view showing an incubator unit.
Figure 3:
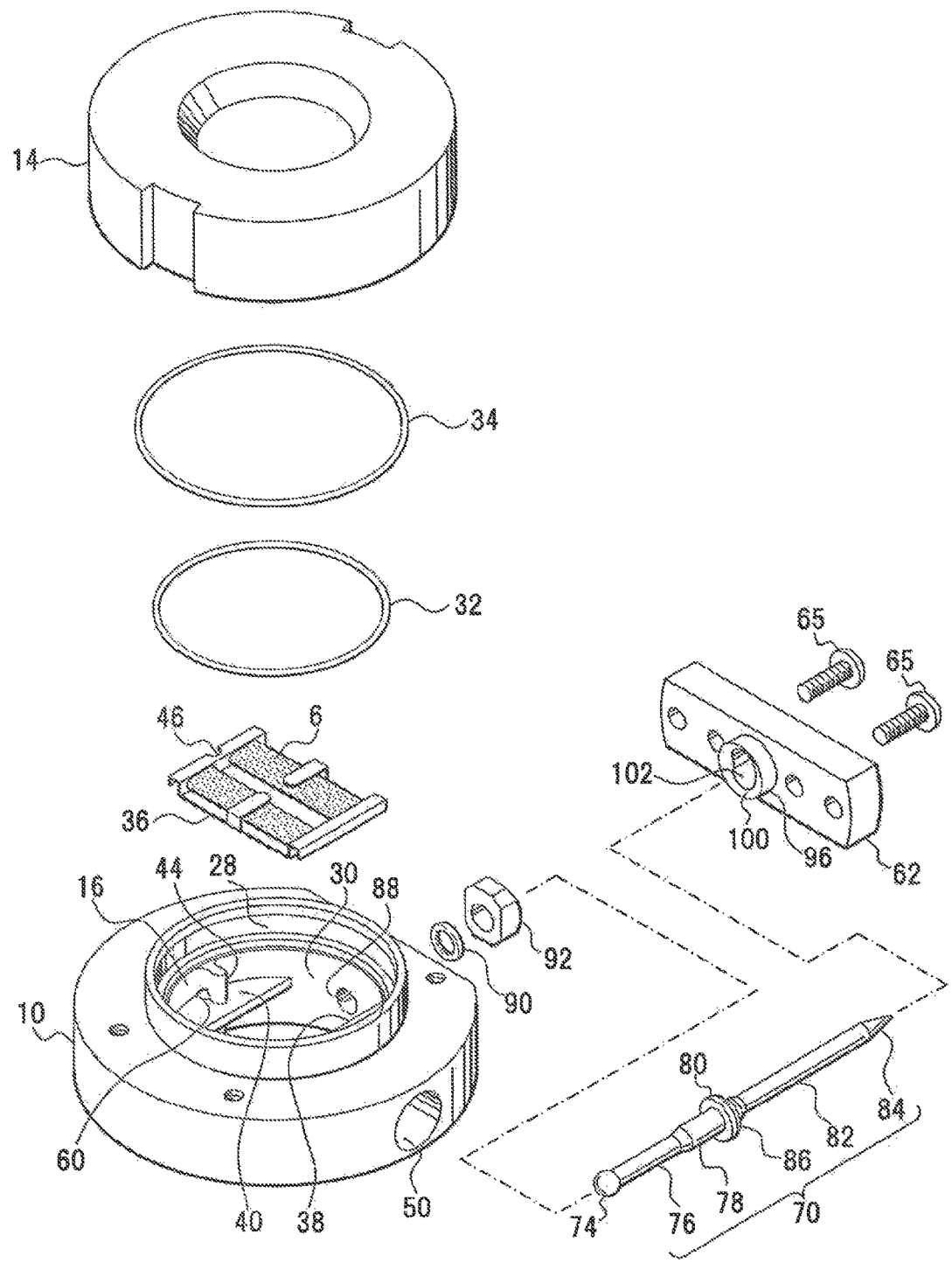
FIG. 3 is an exploded perspective view showing of an incubator body including a cover unit.
Figure 4:
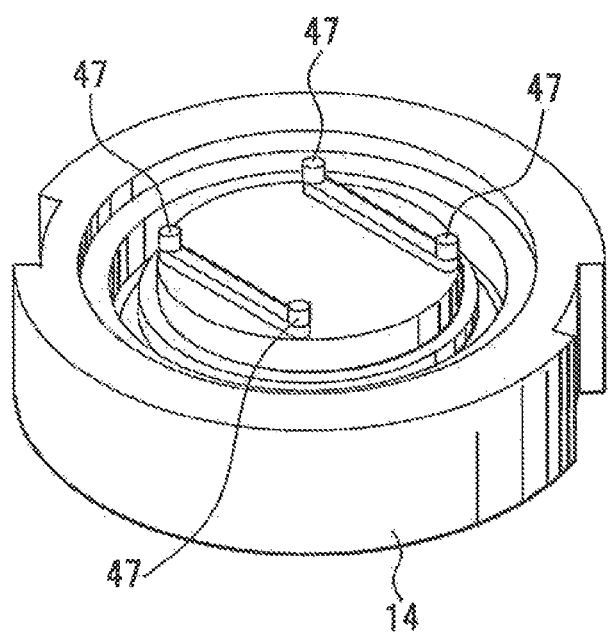
FIG. 4 is a perspective view showing a bottom surface of a cover unit.
Figure 5:
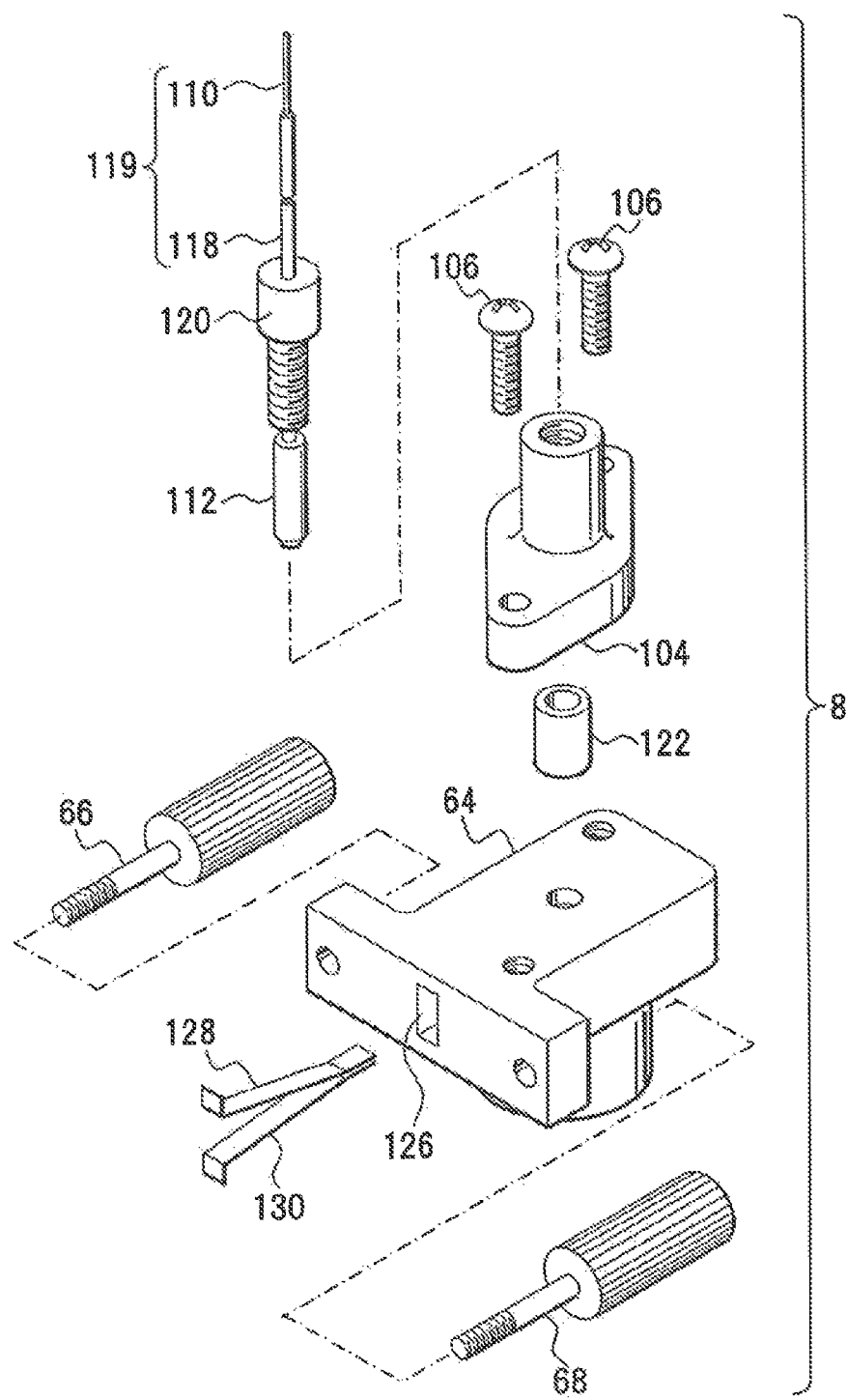
FIG. 5 is an exploded perspective view showing a driving unit.
Figure 6:
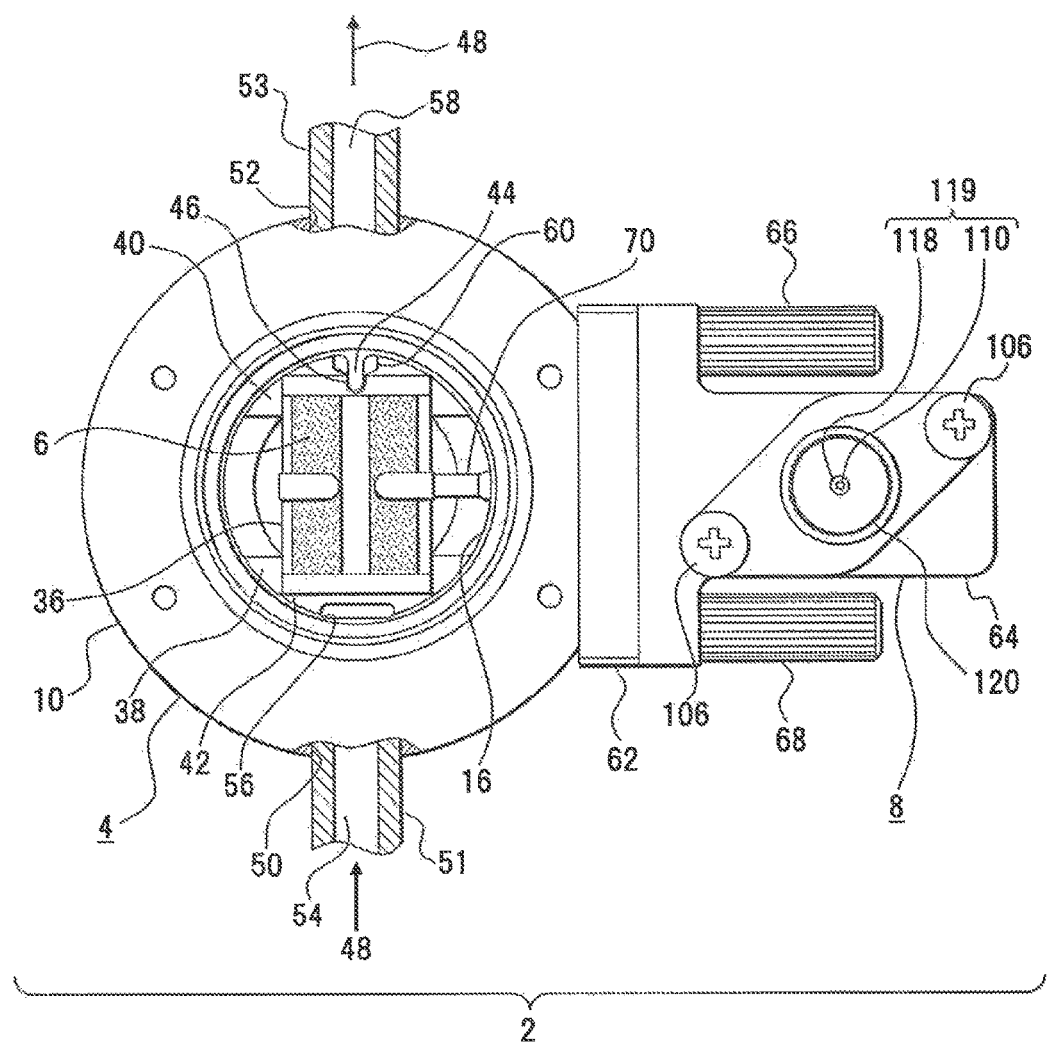
FIG. 6 is a plan view showing a culture unit in a state where a cover unit is taken off from an incubator unit.
Figure 7:
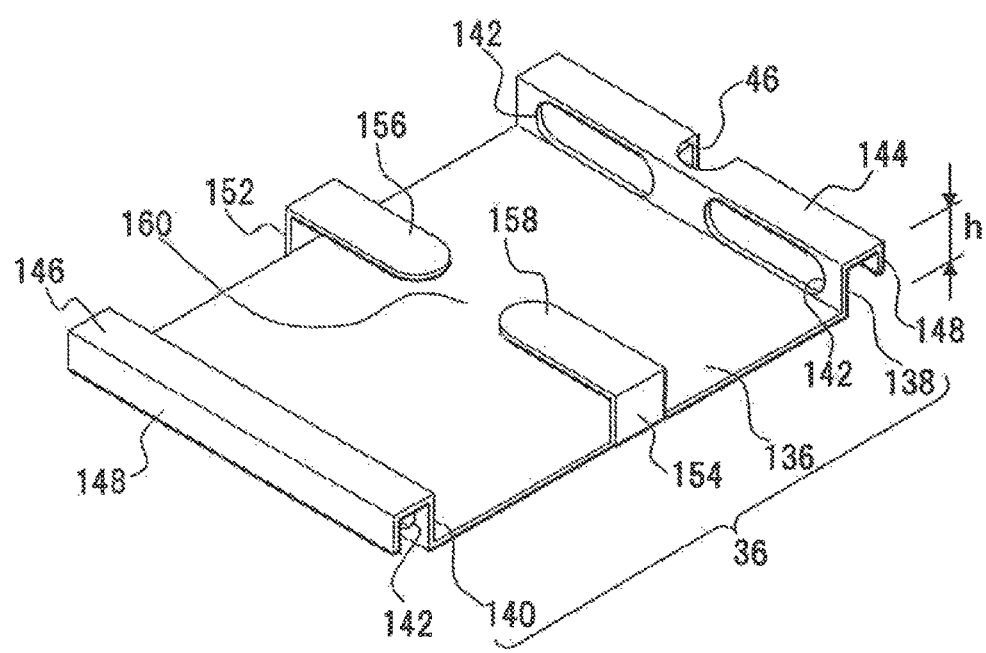
FIG. 7 is a perspective view showing an enlarged culture bed.
Figure 8:
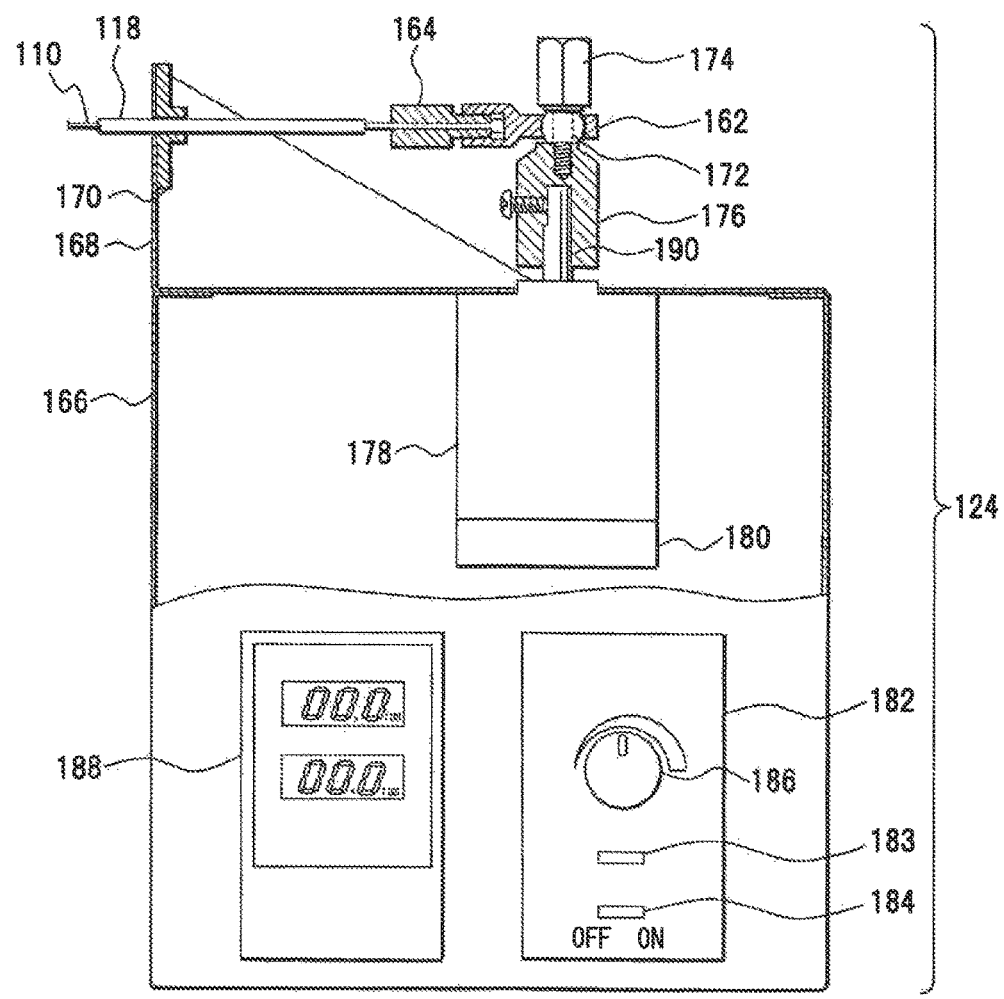
FIG. 8 is a view showing an actuator.
Figure 9:
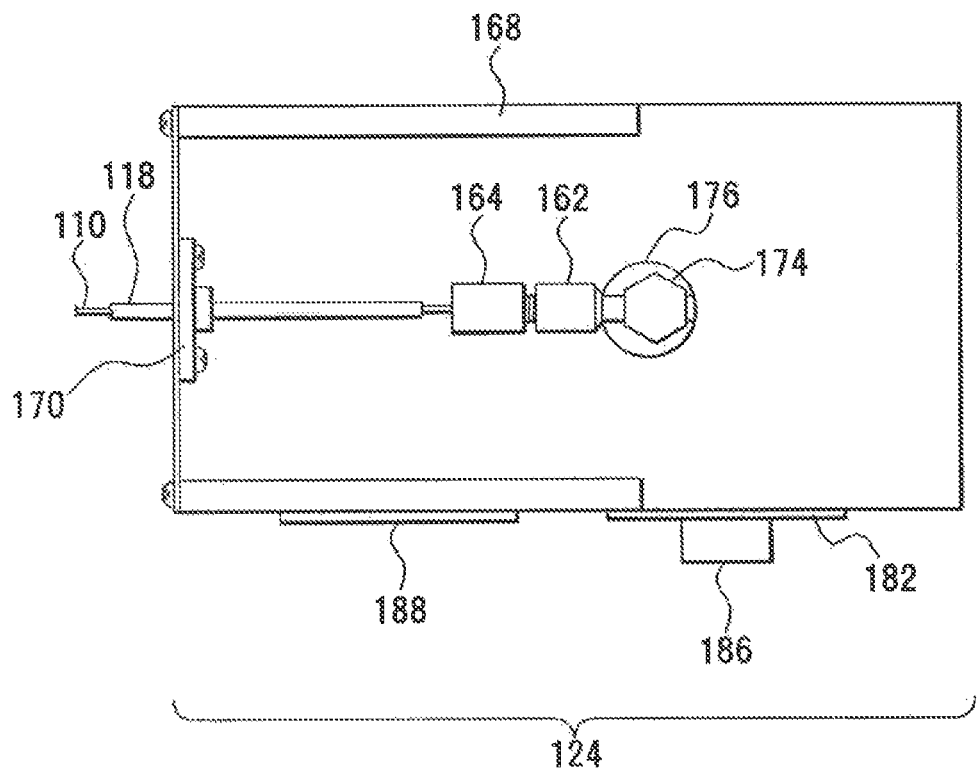
FIG. 9 is a plan view showing an actuator.
Figure 10:
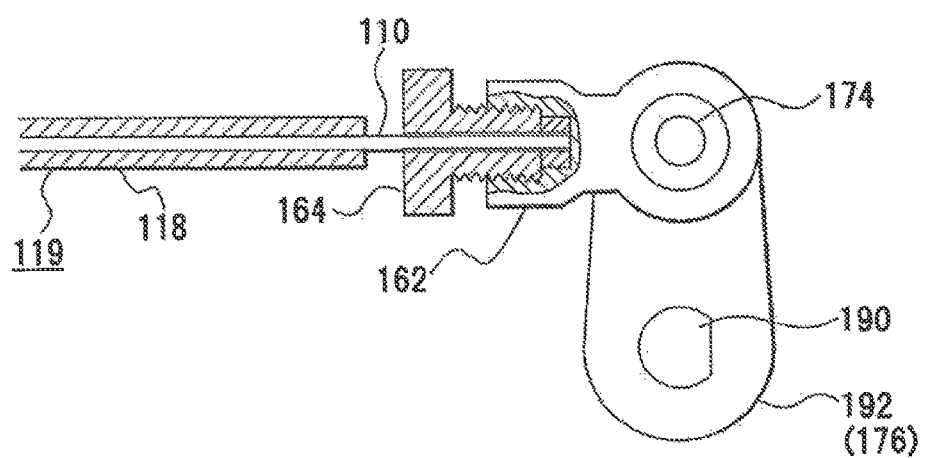
FIG. 10 is a view showing one example of a movement converting unit in an actuator.
Figure 11:
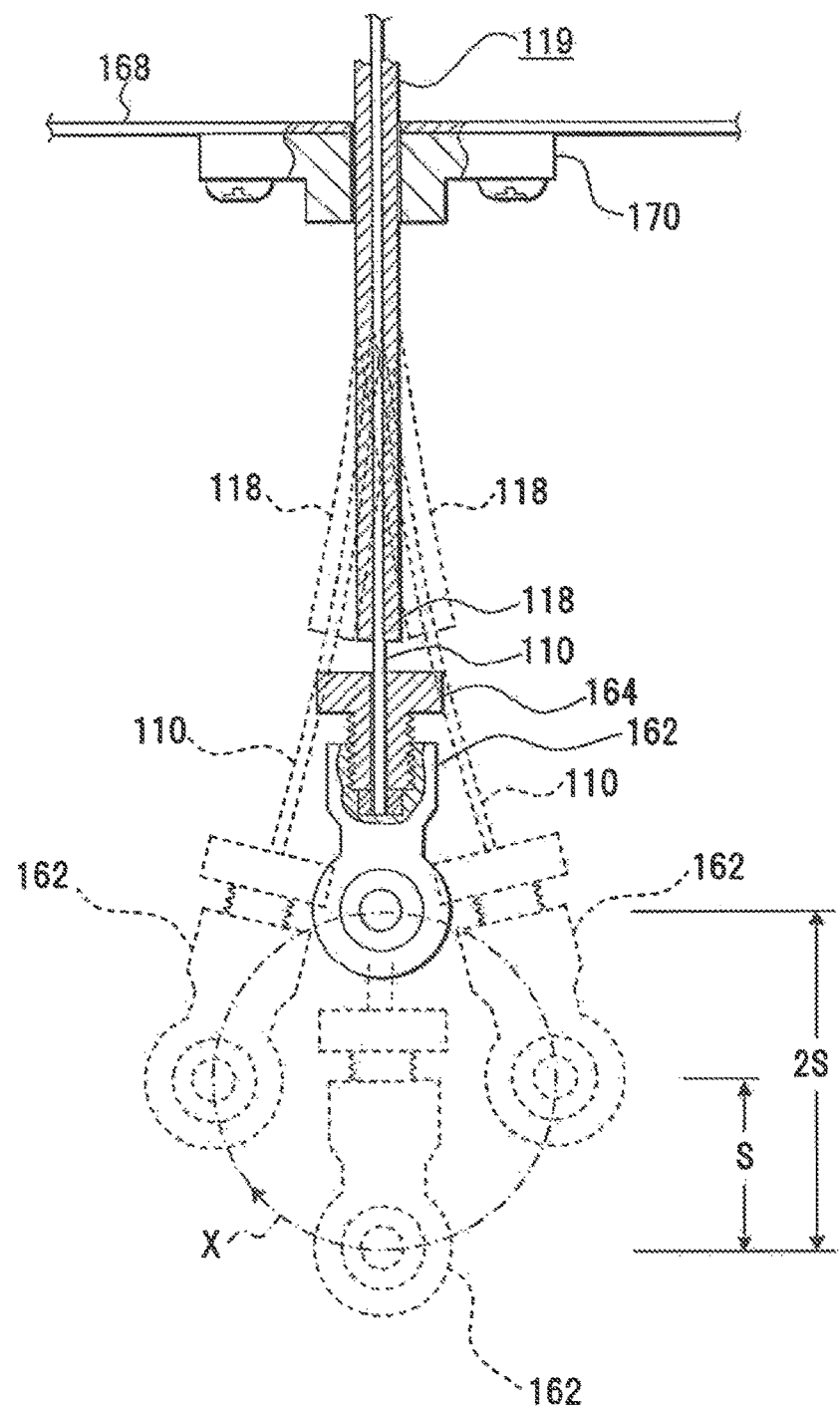
FIG. 11 is a view showing one example of motion of a movement converting unit.
Figure 12:
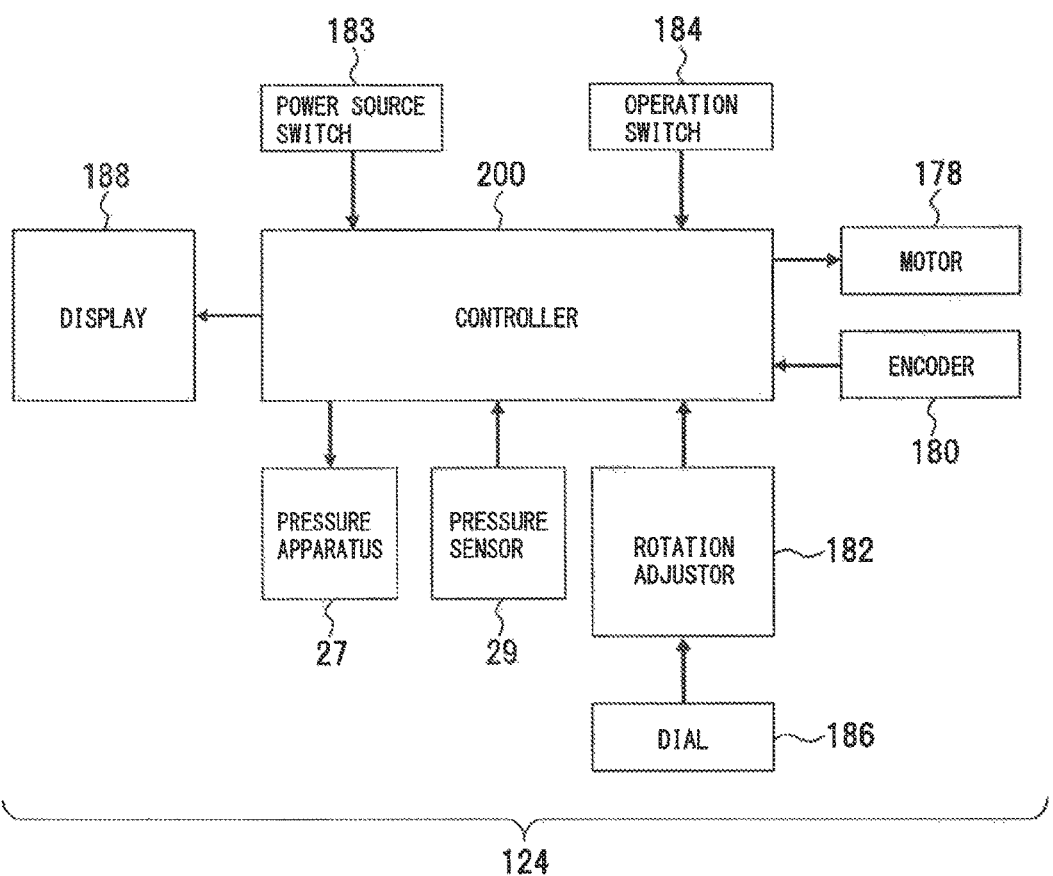
FIG. 12 is a block diagram showing one example of a control system of a cultivation apparatus.

A first embodiment of the present invention will be described with referring to FIGS. 1 to 12. FIG. 1 is a vertical sectional view showing a culture unit according to a first embodiment of a cultivation apparatus, FIG. 2 is an exploded perspective view showing an incubator unit, FIG. 3 is an exploded perspective view showing of an incubator body including a cover unit, FIG. 4 is a perspective view showing a bottom surface of a cover unit, FIG. 5 is an exploded perspective view showing a driving unit, FIG. 6 is a plan view showing a culture unit in a state where a cover unit is taken off from an incubator unit, FIG. 7 is a perspective view showing an enlarged culture bed, FIG. 8 is an elevation view showing an actuator, FIG. 9 is a plan view showing an actuator, FIGS. 10 and 11 depict a concrete example of a movement converting unit in an actuator, and FIG. 12 depicts one example of a control system of a cultivation apparatus. In FIGS. 10 and 11, the same components as an actuator of FIGS. 8 and 9 are denoted by the same reference numerals.

This first embodiment shows a culture unit that imparts bending displacement to a cell construct which is a culture. This culture unit 2 includes, as shown in FIG. 1, an incubator unit 4 as a culture chamber and a driving unit 8 that imparts desired movement to a culture in the incubator unit 4, for example, a cell construct 6. Structure and a function of each function unit will be described, and a cultivation method will be referred as follows.

A) Incubator Unit (Culture Chamber) 4

The incubator unit 4 is a culture space for the cell construct 6, and is a function unit of imparting a culture fluid 48 (FIG. 6), and displacement or stimulation that is necessary for cultivation to the cell construct 6. Then, this incubator unit 4 includes, as shown in FIG. 2, an incubator body 10, an incubator bottom 12 and a cover unit 14. The incubator body 10 is, for example, a flat barrel, and forms a cylindrical culture space 16.

The incubator bottom 12 includes a diaphragm 20 that closes the culture space 16, and is attached to a bottom surface of the incubator body 10 by a plurality of fixing screws 23 through the medium of a sealing means, for example, an O-ring 22. The diaphragm 20 is disposed for applying pressure to the culture space 16 from an outside. A barrel-shaped standing wall 24 is formed on a part of the incubator bottom 12, the part corresponding to the culture space 16. A window 26 enclosed by the standing wall 24 is formed. A pressure sensor 29 is disposed along with a pressure apparatus 27. The pressure apparatus 27 applies pressure P to the culture space 16 via the diaphragm 20 by the medium of a fluid such as water. This pressure P is detected by the pressure sensor 29.

On the top of the incubator body 10, as shown in FIG. 3, a window 30 is formed by a barrel-shaped standing wall 28. O-rings 32 and 34 are intervened inside and outside the standing wall 28 respectively, and thereby, the cover unit 14 is attachably and detachably installed to the incubator body 10.

In an inner wall surface of the culture space 16 of the incubator body 10, shelves 38 and 40 are formed. A culture bed 36 is disposed over both of the shelves 38 and 40. In the incubator body 10, positioning protrusions 42 and 44 (FIG. 6) are formed for the culture bed 36. An edge of the culture bed 36 is touched to one positioning protrusion 42, and the other positioning protrusion 44 is engaged with an engaging concave 46 of the culture bed 36. Thereby, the culture bed 36 is positioned at a predetermined position in the culture space 16, and is held attachably and detachably. That is, a position in height of the culture bed 36 is determined by the selves 38 and 40. A position in a horizontal direction and an angle thereof are determined by positions of the positioning protrusion 42 and the culture bed 36, positional relationship between the positioning protrusion 44 and the engaging concave 46, and engagement therewith.

The culture bed 36 is also held in a vertical direction of the culture space 16. As shown in FIG. 4, on a bottom face of the cover unit 14, a plurality of supporting protrusions 47 that protrude to the culture bed 36 are formed. These supporting protrusions 47 contact an edge of the culture bed 36, and hold the culture bed 36. Thus, free movement of the culture bed 36 in a vertical direction is prevented.

In the incubator body 10, as shown in FIG. 6, an inlet port 50 that runs in the culture fluid 48 to the culture space 16, and an outlet port 52 that exhausts the culture fluid 48 from the culture space 16 are formed. A penetration hole 54 in the inlet port 50 is opened at the bottom of the shelf 38 that the culture bed 36 is disposed, and communicates with a through hole 56 that opens in the positioning protrusion 42. A penetration hole 58 in the outlet port 52 is opened at the bottom of the shelf 40 that the culture bed 36 is disposed, and communicates with a through hole 60 that opens in the shelf 40. Therefore, the culture fluid 48 supplied from the inlet port 50 runs under the shelf 38, runs over the culture bed 36 from the through hole 56 of the positioning protrusion 42, and reaches the penetration hole 58 via an inside of the culture space 16. A part of the culture fluid 48 reaches the outlet port 52 from the top of the culture bed 36 via the through hole 60 of the shelf 40. A circulation pipe 51 is connected to the inlet port 50, and a circulation pipe 53 is connected to the outlet port 52. These circulation pipes 51 and 53 compose a circulation path for the culture fluid 48.

To the incubator body 10, as shown in FIGS. 1, 2, 3 and 6, a joint part 62 is fixed by attachment screws 65. Between the culture space 16 and the driving unit 8, a lever 70 is disposed across the wall of the incubator body 10. This lever 70 can rotate in a circular arc around a fulcrum 72 (FIG. 1) as a center, the fulcrum 72 being set at the wall of the incubator body 10. By driving force imparted by the driving unit 8, a tip of the lever 70 moves up and down. By contacting the tip of the lever 70 on the culture bed 36, the culture bed 36 can be curved, and displacement motion can be imparted to the cell construct 6 that is held by the culture bed 36.

The lever 70 includes, as shown in FIG. 3, an action part 74, a smaller diameter part 76, a larger diameter part (sealing part) 78, a flange 80, a cylinder 82 and a cone 84 whose tip is the sharpest part in the lever 70 in order from the culture space 16 side. The flange 80 has a flat face at a front side when seeing from the action part 74 side, and has a sliding face 86 formed by a sphere at a rear side.

A penetration hole 88 for penetrating the lever 70 is formed in the incubator body 10. The penetration hole 88 is formed in a larger diameter at the culture space 16 side than that at an opposite side for allowing the lever 70 at the culture space 16 to rotate. In order to maintain airtightness between the lever 70 and the wall of the incubator body 10, an O-ring 90 is provided. The center of the O-ring 90 is the center of rotating of the lever 70, and constitutes the above described fulcrum 72. Between the O-ring 90 and the flange 80 of the lever 70, an annular lever guide 92 is disposed. The lever 70 is constituted to rotating around the center of the O-ring 90 as a center of rotating.

The joint part 62 is a member for connecting a frame 64 of the driving unit 8 to the incubator body 10. As shown in FIG. 6, the joint part 62 is fixed by attachment screws 66 and 68. A projection 96 (FIG. 3) of the joint part 62 is engaged with a concave 98 (FIG. 1) corresponding to the penetration hole 88. On the projection 96, a sliding face 100 that contacts the sliding face 86 of the flange 80 of the lever 70 and is formed by a sphere is formed. In the joint part 62, a through hole 102 that has a larger diameter at an opening side than that at an opposite side for allowing the lever 70 to rotate is formed.

In the incubator unit 4, the diaphragm 20 is, for example, formed by a flexible material such as silicone rubber that does not liquate out and is high safety. The diaphragm 20 is formed into a thin shape, and the O-ring 22 is formed thereround. The reason why the diaphragm 20 is a thin membrane is for transmitting outside pressure P into the culture space 16, and for making pressure in the incubator unit 4 almost the same pressure as pressure in an area beyond the diaphragm 20. The lever 70 is sealed by the O-ring 90, then airtightness and water-tightness of the incubator body 10 are maintained.

B) Driving Unit 8

The driving unit 8 is a function unit that receives driving force imparted from an outside, and drives the lever 70 imparting displacement motion to the cell construct 6. To the frame 64 of the driving unit 8, as shown in FIGS. 1 and 5, the cover part 104 is fixed by a plurality of screws 106. The cover part 104 receives driving force via a wire 110. To the cover part 104, a first slider 112 that moves up and down is slideably attached. A tip of the slider 112 touches on the lever 70. In the frame 64, a second slider 114 that is disposed on the same line as the slider 112 is provided. Between the slider 114 and the frame 64, provided is a spring 116 that acts restoring force on the slider 114 to move the slider 114 upward. The spring 116 composes a restoring spring that replaces the slider 112 to a position before movement.

The wire 110 is attached at its tip to the slider 112. An outer tube 118 is provided around an outside face of the wire 110. The wire 110 is slideable independently from the outer tube 118. A cable 119 is composed of the wire 110 and the outer tube 118. The outer tube 118 penetrates a fixing nut 120, and is fixed to the cover part 104 by the fixing nut 120. Between the fixing nut 120 and the cover part 104, a sliding bush 122 is disposed. An actuator 124 (FIGS. 8 and 9) is attached to an edge of the wire 110 as a driving source for moving the slider 112 up and down. In this case, if the slider 112 falls, the slider 114 is pressed down along with the lever 70, and if driving force of the actuator 124 is released, the sliders 112 and 114 restore to original positions by restoring force of the spring 116.

In the frame 64, an opening 126 for inserting the lever 70 is formed. Guide plates 128 and 130 that guide insertion of the lever 70 are inserted between the sliders 112 and 114 from the opening 126. If the cone 84 of the lever 70 is inserted between the guide plates 128 and 130, the lever 70 can be easily inserted into a predetermined position between the sliders 112 and 114.

C) Culture Bed 36

The culture bed 36 is a means for holding the cell construct 6 and for transmitting displacement motion to the cell construct 6, and is a function unit returning the cell construct 6 to a state before displacement motion by using elasticity that the culture bed 36 has. The culture space 16, for example, accommodates the cell construct 6 disposed on the culture bed 36.

A disposing part 136 where two cell constructs 6 are disposed in parallel is included in the culture bed 36 as shown in FIG. 7. This disposing part 136 constitutes a receiving part that is deformed by receiving action from an outside, has an area and a shape for disposing two cell constructs 6 in parallel, and is made in a plate form from an elastic member for imparting bending motion to each cell construct 6. As an elastic member, for example, a stainless steel sheet for a spring or other materials that have high spring are used. In this case, the whole culture bed 36 may be formed by an elastic member, or the disposing part 136 that enables bending motion or a part of the disposing part 136 may be formed by an elastic member. The deposing member 136 is not limited to a flat-plated shape, and may be net. Stable coating may cover the disposing part 136 to prevent component of a spring member from liquating out.

The disposing part 136 is a rectangular shape. At end parts in a longer direction thereof, rectangular standing walls 138 and 140 are formed. Each of the standing walls 138 and 140 is perpendicular to the disposing part 136, and in the standing walls 138 and 140, elliptic through holes 142 where each cell construct 6 is inserted are formed. These through holes 142 have a role of fixing both ends of the cell construct 6. Each of the standing walls 138 and 140 is set in a predetermined height h according to a size of each cell construct 6.

At a top of each of the standing walls 138 and 140, supporting faces 144 and 146 that have a constant width in parallel to the disposing part 136 and are formed. From each supporting face 144 and 146, a turnover 148 is formed in parallel to each of the standing walls 138 and 140 by turning apart of each supporting face 144 and 146. Each turnover 148 reinforces each supporting face 144 and 146, and each standing wall 138 and 140, and fixes the cell construct 6. That is, sufficient strength can be obtained if each supporting face 144 and 146, and each standing wall 138 and 140 are formed by the same board as the disposing part 136 which is made of a thin plate, and, in the embodiment, the culture bed 36 is bent only in a longitudinal direction. In the culture bed 36, the U-formed engaging concave 46 corresponding to the positioning protrusion 44 as shown in FIG. 6 is formed in order to fix the supporting face 144.

From middle edges of the disposing part 136, supporting walls 152 and 154 that support sides of the disposed cell construct 6 are formed. From a top of each supporting wall 152 and 154, holding parts 156 and 158 that cover a top surface of the cell construct 6 are formed. Each supporting wall 152 and 154 is a wall perpendicular to the disposing part 136. The height thereof is the same as the above described standing walls 138 and 140. Each holding part 156 and 158 constructs a parallel face with the disposing part 136. The cell construct 6 is disposed in a gap between the disposing part 136, and each holding part 156 and 158. An end part of each holding part 156 and 158 constructs a curve face. Between the end parts, a gap 160 for attaching and detaching the cell construct 6 is set.

Concerning the incubator unit 4, components thereof are selected in view of stability, economics, sterilizationproof, workability, abrasion resistance, handleability, etc. for a culture and a culture fluid. For components of contacting the culture fluid 48, for example, the incubator body 10, the cover unit 14, the O-rings 32, 34 and 90, the culture bed 36 and the lever 70, a material of high stability that does not liquate out must be used. For example, stainless steel, plastic, etc. can be used. Stainless steel is superior in stability and sterilizationproof, and plastic is superior in workability and handleability such as weight saving and disposability.

If plastic is used, disposable use can be performed for a need of preventing pollution by germs and pollution by a cell or a gene of another person. Plastic is cheaper than stainless steel. The incubator unit 4 must be sterilized in an assembled state. Both stainless steel and plastic are proof against damage from a sterilization process. For example, full heatproof characteristic is requested in an autoclave that executes a sterilization process on condition of 121° C. and 2 pressure. For such process, fluororesin such as PTFE, ETFE and PFA, polysulfane, polyethersulfane, polycarbonate, PET and polyethersulfane reinforced by glass, etc. are suitable. For a sterilization process by a γ-ray or an electronic ray, ETFE, polysulfane, polyethersulfane, polycarbonate, PET, polyethylene, polypropylene, etc. are suitable.

In the incubator unit 4, abrasion resistance is requested because sliding of the flange 80 of the lever 70 is repeated at the joint part 62 and the lever guide 92, etc. Then, fluororesin such as polyacetal, polyethylene, polypropylene, PTFE, ETFE, and PFA is suitable.

For observing an inside of the cover unit 14 without taking off the cover unit 14, a transparent material is suitable. For the cover unit 14, a transparent material such as polysulfane, polyethersulfane, polycarbonate, PET, etc. are suitable.

In order to prevent pollution of a culture, a sterilization process is necessary. Selection of a material in view of proof to sterilization is important. The best materials that endure a sterilization by both of an autoclave and a γ-ray or an electronic ray are as follows in view of functionality, etc. that each component needs.

For the incubator body 10, the incubator bottom 12 and the cover unit 14, polysulfane, polyethersulfane or polycarbonate is suitable. For the O-rings 32, 34 and 90, fluororubber or silicone rubber is suitable. For the diaphragm 20 and the O-ring 22, fluoro-rubber, silicone rubber or an ETFEE film is suitable. For the joint part 62 and the lever guide 92, ETFE is suitable. For the lever 70, stainless steel (SUS316 and SUS304) is suitable. For the culture bed 36, stainless steel for a spring (a series of SUS304CSP) is suitable.

Stainless steel for a spring is less corrosion resistance than a series of SUS316. For supplement this less corrosion resistance, for example, coating such as diamond-like coating (DLC) may be covered.

If reusing is expected with washing carefully, instead of plastic, stainless steel SUS316 or SUS304 may be used. As to a component material of the culture bed 36, a function of occurring displacement movement by applying pressure and returning to a state before displacement is necessary. So, for example, a hard elasticity member such as stainless steel for a spring may be used.

D) Actuator 124

The actuator 124 constitutes a driving source that imparts driving force of the lever 70 from an outside to the driving unit 8. As shown in FIGS. 8 and 9, the actuator 124 converts rotation of a motor to back and forth move of the wire 110, and applies move thereof to the slider 112 of the driving unit 8. The wire 110 of the driving unit 8 is guided to the actuator 124 along with the outer tube 118, and the tip of the wire 110 is fixed to a crank lever 162 by a wire fixing screw 164. The outer tube 118 that covers the wire 110 is fixed to a fixing part 170 of a reinforcing plate 168 that is disposed on the frame 166 of the actuator 124 as a relay member.

The crank lever 162 is fixed to a crank shaft 174 via a baring 172. A motor 178 is attached to a crank 176 where the crank shaft 174 is fixed. The motor 178 is, for example, constituted of a DC motor. With this motor 178, an encoder 180 that detects rotation is disposed.

A rotation adjuster 182, a power source switch 183, an operation switch 184, a rotation adjusting dial 186 and a display 188 that displays number of rotations, etc. are disposed on the frame 166 of the actuator 124.

As an example showing an enlarged crank mechanism of this actuator 124, as shown in FIG. 10, a crank arm 192 showing the crank 176 is attached to a rotation shaft 190 of the motor 178. To the crank arm 192, the crank lever 162 is rotatably attached by the crank shaft 174. To the crank lever 162, the tip of the wire 110 is fixed by the wire fixing screw 164.

According to such structure, by rotation of the motor 178, the crank arm 192 rotates around the center of the rotating shaft 190. The crank lever 162 that is attached to a tip of the crank arm 192 by the crank shaft 174 moves as writing a track shown by a dotted and dashed line X in FIG. 11. The wire 110 that is fixed to the tip of the crank lever 162 moves back and forth correspondingly to a stroke 2S according to length S of the crank arm 192, and this displacement movement is imparted to the driving unit 8 via the wire 110. This displacement movement is transmitted to the lever 70, and makes the lever 70 move like a circular arc.

There is no need to rotate the crank arm 192 sequentially. If the crank arm 192 is displaced by a necessary angle with using a stepper motor or a servo motor, displacement movement of the lever 70 can be obtained as well.

With the actuator 124, as shown in FIG. 12, a controller 200 that controls the motor 178 is provided. To the controller 200, the pressure apparatus 27, the pressure sensor 29, the motor 178, the encoder 180, the rotation adjustor 182, the power source switch 183, the operation switch 184, the display 188, etc. are connected. In the controller 200, rotational speed is set to the rotation adjustor 182 by the rotation adjustment dial 186. Rotation of the motor 178 is set to set rotational speed. This rotational force is converted to back and forth movement of the wire 110 to be imparted to the driving unit 8. Rotation of the motor 178 is detected by the encoder 180, difference between rotational speed of the motor 178 and set rotational speed is calculated, and the motor 178 is controlled in a predetermined rotational speed. In this embodiment, by using the controller 200, output pressure P of the pressure apparatus 27 is controlled in accordance with detected pressure of the pressure sensor 29.

Another controller may control the pressure apparatus 27, or take in detected pressure of the pressure sensor 29.

E) Cultivation Method

Figure 13:
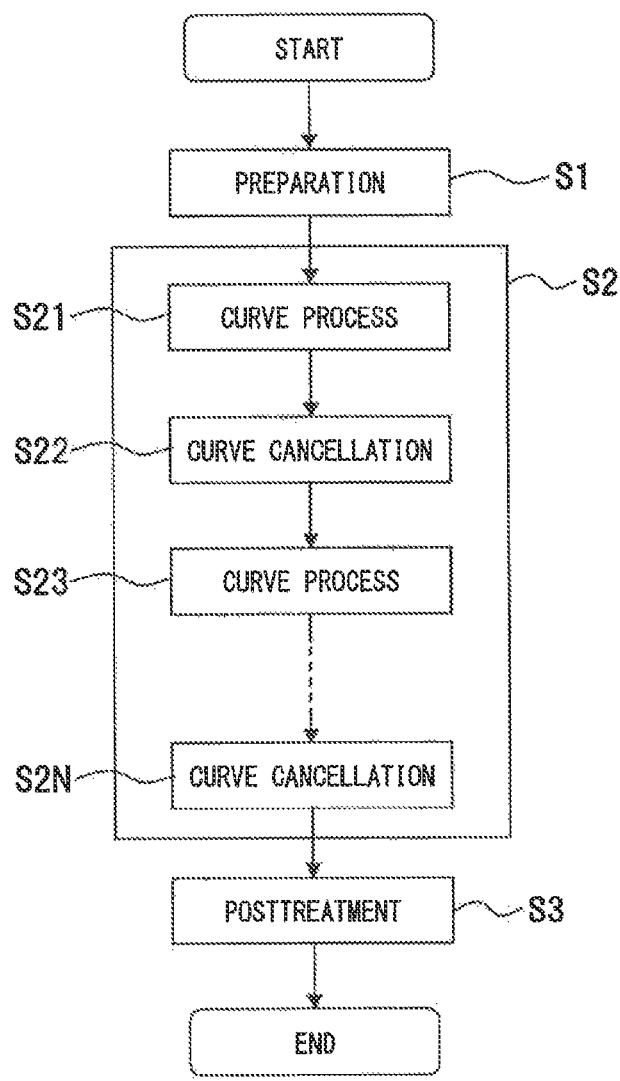
FIG. 13 is a flowchart showing processing procedure of cultivation.
Figure 16:
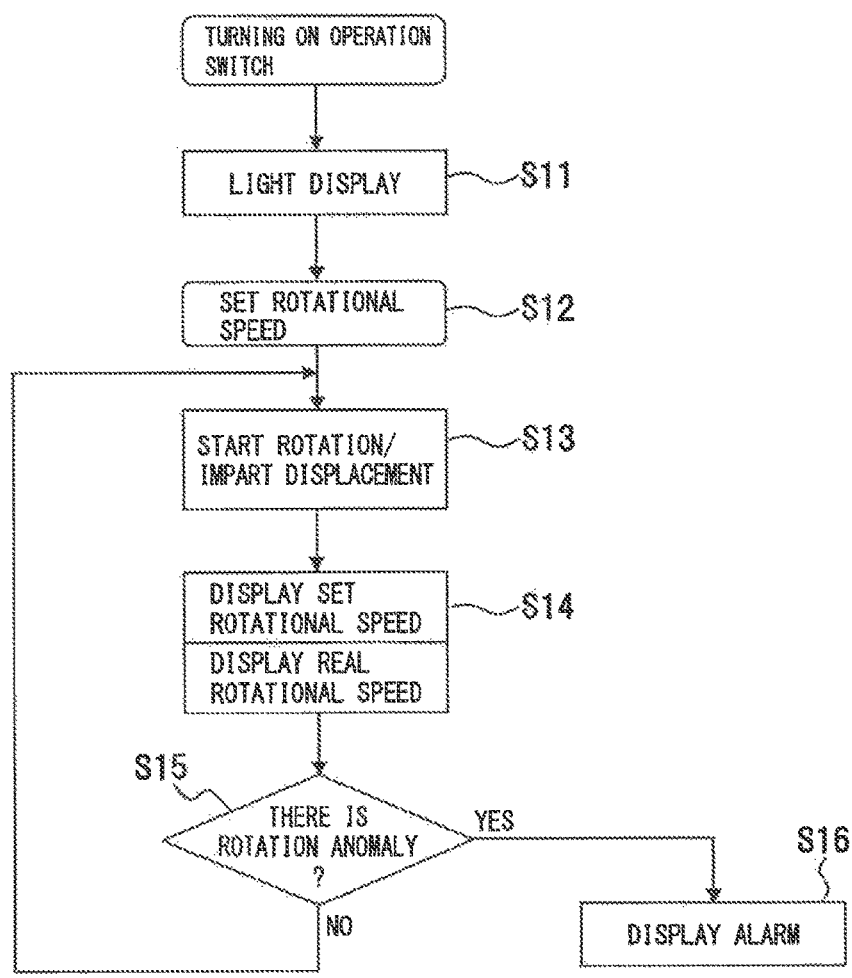
FIG. 16 is a flowchart showing operation procedure of an actuator.

A cultivation method for a cell or tissue by using the culture unit 2 will be described with referring to FIGS. 13-16. FIG. 13 is a flowchart showing processing procedure of cultivation, FIGS. 14A and 14B depict disposing the cell construct, FIGS. 15A and 15B depict imparting bending motion to the cell construct and cancellation thereof, and FIG. 16 is a flowchart showing operation procedure of the actuator.

As shown in FIG. 13, a cultivation process of the cell construct 6 includes a preparation (step S1), a cultivation process (step S2) and a posttreatment (step S3). The preparation includes processes of forming the cell construct 6, a wrapping in a semi-permeable membrane, etc. The cultivation process includes a bending movement process. In the cultivation process, a curve process (step S21), curve cancellation (step S22), a curve process (step S23) . . . curve cancellation (step S2N) are repeatedly executed. The posttreatment includes taking out of the cell construct 6 whose cultivation is ended from the culture bed 36.

I Preparation (Step S1)

Figure 14A:
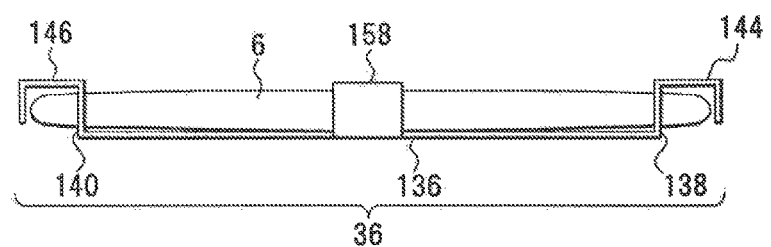
FIG. 14A is a view showing a culture bed where a cell construct is disposed.
Figure 14B:
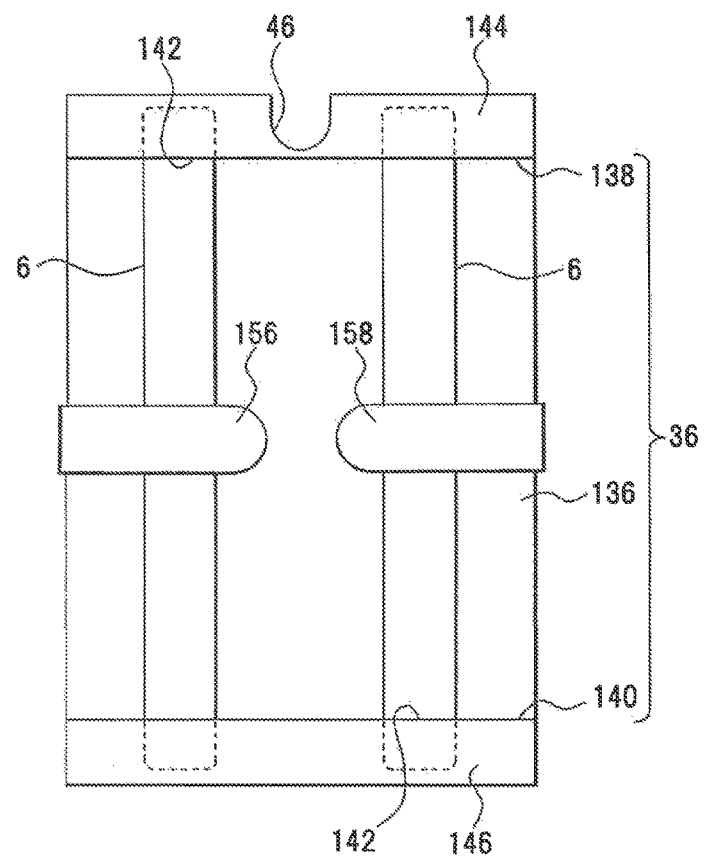
FIG. 14B is a view showing a culture bed where a cell construct is disposed.

As shown in FIGS. 14A and 14B, the cell construct 6 that is a culture is formed. This cell construct 6 is, for example, covered by a semi-permeable membrane.

The cell construct 6 includes one or some of a cell, a cell scaffold, an extracellular matrix generated by the cell and the culture fluid 48. Additives may be included as other elements.

The cell construct 6 may be a three dimensional scaffold where cells are disseminated and a gel substance, be a three dimensional scaffold where cells are disseminated being sealed by a semi-permeable membrane, or be a three dimensional scaffold where cells are disseminated and a gel substance, both of which is sealed by a semi-permeable membrane. A three dimensional scaffold and a gel substance are composed of a bioabsorbable material.

The cell construct 6 also may be a three dimensional scaffold where cells are disseminated, be a complex of the construct and other scaffolds, be the above inserted into a bag or a tube of a semi-permeable membrane, be a culture fluid where cells are suspended being enclosed in a bag or a tube of a semi-permeable membrane, or be cells and a gel scaffold being enclosed into a bag or a tube of a semi-permeable membrane.

A semi-permeable membrane may be selected out of semi-permeable membranes whose transmission molecular weight is from 100 (Da) to 1000 (kDa), and a selected semi-permeable membrane may be used. An idea of using a semi-permeable membrane in cultivation is described in PCT/US2005/027220 (Amorphous cell delivery vehicle treated with physical/physicochemical stimuli), etc. Since various kinds of semi-permeable membrane are provided in accordance with a size of a molecule that can pass through the semi-permeable membrane, the membranes may be used. That is, if a semi-permeable membrane such that substance of a low molecule like nutrition, a necessary gas such as oxygen and waste matters exhausted by a cell in a culture fluid passes, and a cell and a polymeric extracellular matrix are not allowed to pass is selected then cells are closed, nutrition and oxygen can be supplied while preventing an outflow of a cell and an extracellular matrix, and effective cultivation is realized. In this case, as a measure against a case where a semi-permeable membrane prevents passage of nutrition, in the present invention, bending movement is added. Thus, displacement of a bending part rises actively, and difference of pressure occurs, thus, move of nutrition is promoted. The cell construct 6 that a blood vessel is still not generated (tissue without a blood vessel) is also cultivated with bending motion that acts for working a blood vessel and a heart, and simultaneously, the bending motion imparts physical stimulation to a cell.

The cell construct 6 covered by a semi-permeable membrane is, as shown in FIGS. 14A and 14B, disposed on the disposing part 136 of the culture bed 36. The cell construct 6 is held by the culture bed 36 and disposed thereon.

II Cultivation Process (Step S2)

The cell construct 6 is, as shown in FIGS. 1 and 15A, transferred to the incubator unit 4 that is a culture space along with the culture bed 36.

The culture fluid 48 is supplied into the incubator unit 4, and the cover unit 14 is attached. After the cover unit 4 is attached, four supporting protrusions 47 that are provided with the cover unit 14 lightly press edges of the culture bed 36 and hold the culture bed 36.

If force F is imparted from a back side of the culture bed 36 by the lever 70, as shown in FIG. 15B, the disposing part 136 of the culture bed 36 is curved upwardly by the force F. By this curving, the cell construct 6 on the disposing part 136 is also curved. That is, bending occurs to the cell construct 6.

If the force F is released from this bending state, the disposing part 136 of the culture bed 36 is restored to an original form by its elasticity to become flat. Thus, as shown in FIG. 15A, the cell construct 6 on the disposing part 136 shifts into a flat state. In this case, on a top face of the cell construct 6, the holding parts 156 and 158 of the culture bed 36 exist. The cell construct 6 that is deformed to be convex upwardly is pressed onto the holding parts 156 and 158 in accordance with restoration of the disposing part 136 to flatten dependently on restoration to an original form of the disposing part 136.

Such bending movement is repeated (step S21-step S2N), and tissue is formed as necessary cultivation time passes. If the culture unit 2 shown in FIG. 1, etc. is used, a desired pressure P can be acted on the cell construct 6 separately from bending by applying the pressure P to the diaphragm 20 of the incubator bottom 12 via the culture fluid 48.

In this cultivation, It is possible to supply the fresh culture fluid 48 to the culture space 16 by supplying the culture fluid 48 from the inlet port 50 to the culture space 16 to be exhausted from the outlet port 52. The culture fluid 48 is a supply medium that supplies gas such as oxygen and a nutrient, etc. to the cell construct 6, and a transmitting medium for transmitting waste matters exhausted from the cell construct 6.

III Posttreatment (Step S3)

The cell construct 6 whose cultivation is completed is taken out from the incubator unit 4 (FIG. 1, etc.) with the culture bed 36. The cell construct 6 is applied to a restoration region of a human being.

In such process procedure of cultivation, control operation of the controller 200 will be described with reference to a flowchart shown in FIG. 16.

If the operation switch 184 is turned on, the display 188 is lighted (step S11), and rotational speed is set in this lighting state (step S12). By this, rotation is started, and displacement is given from the actuator 124 via the wire 110 to the slider 112 of the driving unit 8 (step S13). By back and forth motion of the wire 110, the lever 70 is rotated and the above described movement is imparted to the cell construct 6.

If rotation and displacement are generated, set rotational speed and real rotational speed are displayed on the display 188 (step S14). By the controller 200, rotational speed difference between real rotational speed and set rotational speed is monitored (step S15). If difference in rotational speeds or uneven rotation reach a predetermined value or over the predetermined value, it is detected to be anomaly. If anomaly occurs, an alarm is displayed on the display 188 (step S16).

Second Embodiment

Figure 17:
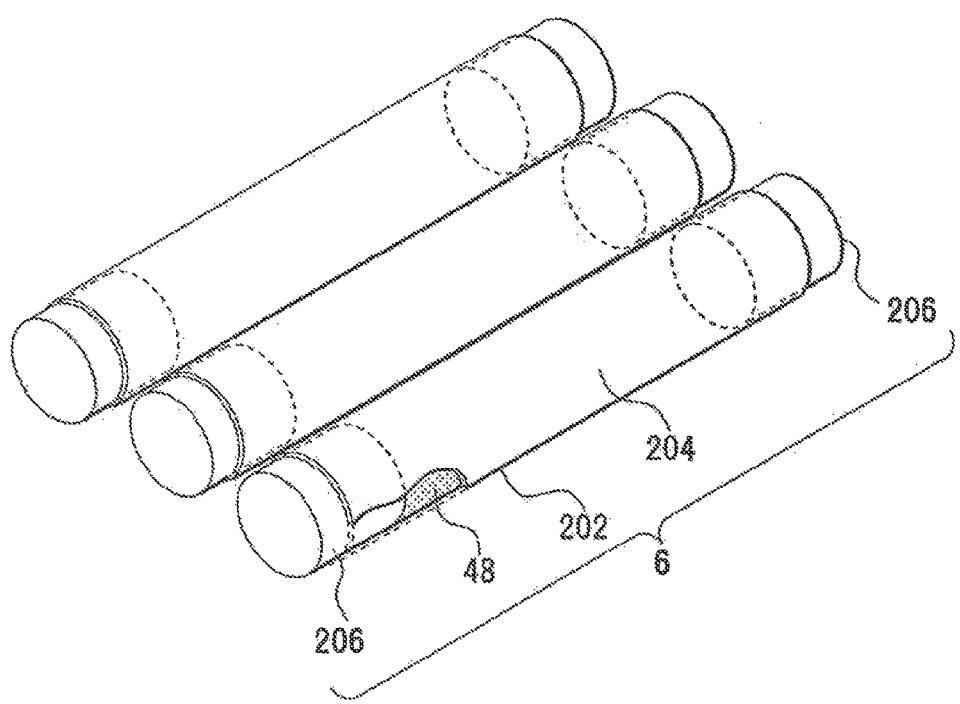
FIG. 17 is a view showing a structural example of a cell construct according to a second embodiment.
Figure 18:
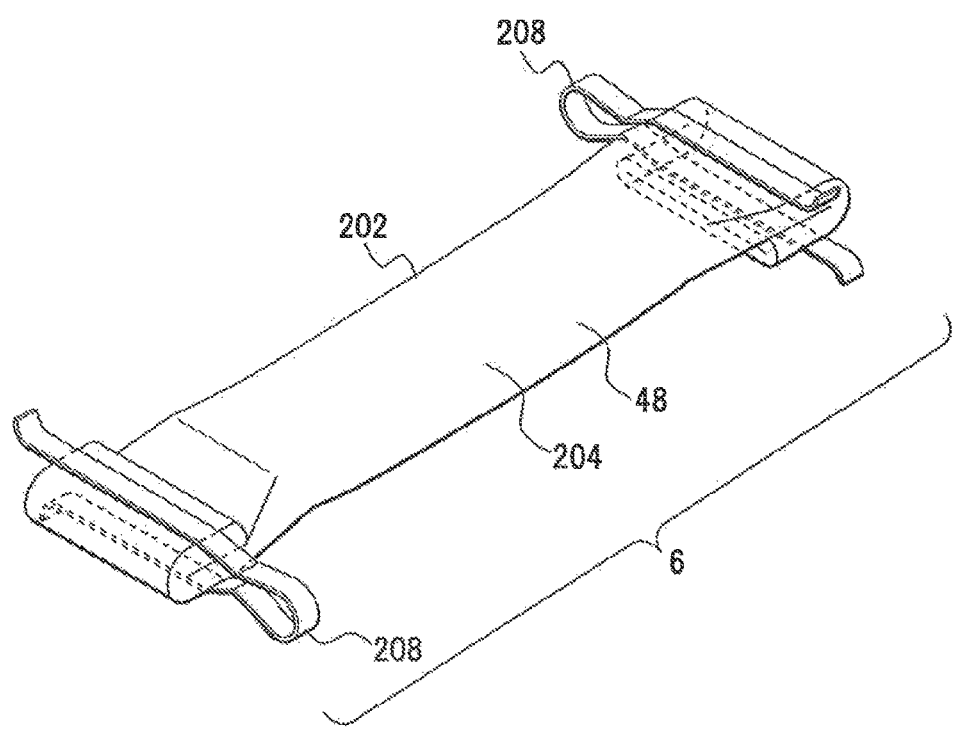
FIG. 18 is a view showing another structural example of a cell construct.
Figure 19:
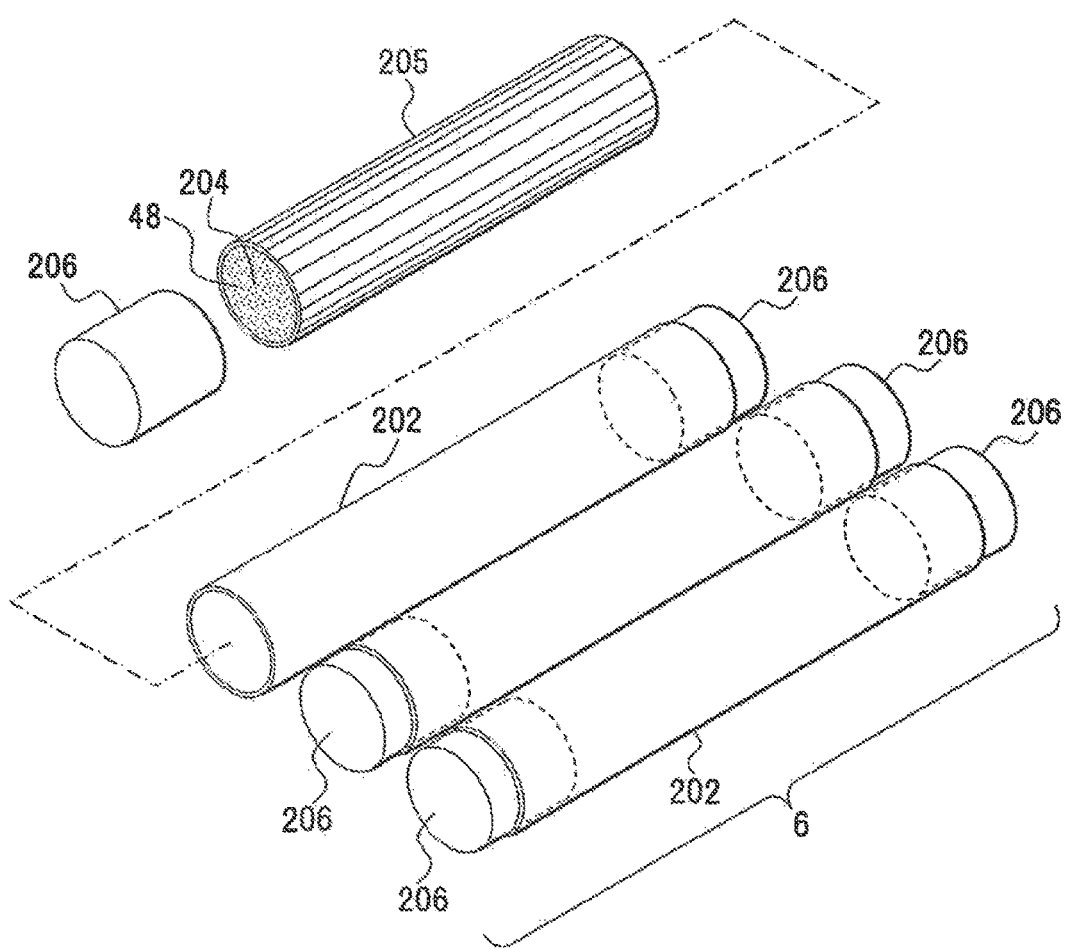
FIG. 19 is a view showing another structural example of a cell construct.

A second embodiment of the present invention will be described with referring to FIGS. 17 to 19. FIGS. 17 to 19 depict a structural example of a cell construct.

Steps of a cultivation method for a cell and/or tissue by using this cell construct are as follows:
a. Tissue or a cell is taken out from in vivo;
b. The taken tissue is resolved by enzymes and so on and a cell is separated to select a necessary cell. Every sort of cells can be cultivated;
c. If the number of selected cells runs short or, must be grown, the number of the cells is once increased by monolayer cultivation and so on;
d. The cell construct is made.
  i. In case of an infinite construct (a growth factor or chemist may be added to one or some of followings if necessary)
    a cell is suspended in a culture fluid
    a cell is suspended in a hydro-gel
    a cell is mixed with a gel scaffold
  ii. In case of a finite construct (a growth factor or chemist may be added to one or some of followings if necessary)
    a cell is suspended in a culture fluid, and the culture fluid is entered into a cell scaffold such as a collagen sponge and a chitosan sponge to attach the cell to the scaffold
    a cell in a sol state is mixed into a scaffold, and the scaffold is entered in a cell scaffold such as a collagen sponge and a chitosan sponge to attach the cell to the scaffold and to gel the cell.
e. A cell construct 6 is configured by entering a cell, etc. in a tube or a bag of a semi-permeable membrane and sealing the tube or the bag. A cell and a high molecular are not transmitted through a semi-permeable membrane, and a low molecular like nutrition, a chemical and gas such as oxygen in a culture fluid are transmitted through a semi-permeable membrane.
f. The cell construct 6 is attached to a culture bed 36.
g. If a culture fluid is circulated, a circulation circuit is prepared for a culture fluid. A gas exchanger is provided with the circulation circuit, and gas in a cultivation apparatus and a gas in a culture fluid of the culture circuit can be exchanged.
h. The cell construct 6 is entered into an incubator unit 4 with the culture bed 36, and a culture fluid 48 is filled.
i. A cover unit 14 is attached to the incubator unit 4, and the incubator unit 4 (and the culture circuit) is sealed. The above are executed in clean environment such as a clean room and clean bench. After that, since the circuit is sealed, pollution by germs does not occur even in other places.
j. A driving unit 8 is attached to the incubator unit 4.
k. Temperature and gas concentration is maintained in the best state.
l. Bending motion is repeatedly imparted to the cell construct 6. A period, size, a motion schedule, etc. of bending motion are set in advance to operate.
m. If necessary, a culture fluid is circulated and pressure is applied. Concerning pressure, the best pattern is selected out of pressure patterns of constant, intermittent, periodical repeat, etc.
n. After a predetermined time passes, the driving unit is taken off from the incubator unit 4.

In such cultivation method, the cell construct 6 is, as shown in FIG. 17, entered into a tube 202 by a semi-permeable membrane. In this case, the cell construct 6 is constituted of the culture fluid 48 and a mixture 204 that gel is mixed with a cell. Openings of both ends of the tube 202 are sealed by a stopper 206.

For example, a pair of cell constructs 6 is attached to the culture bed 36, and the above described bending displacement motion is repeatedly imparted. From this, a cell is propagated, and an extracellular matrix and so on are generated to generate infinite neogenetic tissue.

Seeing this generating process, before cultivation, the cell construct 6 is combination of all or a part of a cell, a culture fluid, a hydro gel and a gel scaffold. After cultivation, the cell construct 6 is converted into combination of all and a part of a cell, a culture fluid, a hydro gel, a gel scaffold, an extracellular matrix or other products of a cell.

If a culture extracted from the cell construct 6 is injected into a damaged or deficit part in vivo, original tissue is regenerated at an injected part. The injected culture amalgamates with tissue therearound and is integrated.

The cell construct 6 is, as shown in FIG. 18, entered into the tube 202 by a semi-permeable membrane. In this case, the cell construct 6 is also constituted of the culture fluid 48 and the mixture 204 that gel is mixed with a cell. Each opening at the edges of the tube 202 is bent, and is sealed by being sandwiched by clips 208. In this case, the tube 202 has room. The culture fluid 48 and the mixture 204 are entered so that a sectional area of the tube 202 that is filled with the culture fluid 48 and a mixture becomes ellipse. These cell constructs 6 are attached to the above described culture bed 36, and repeatedly curved.

By using such cell constructs 6, a cell is propagated, and an extracellular matrix and so on are generated to generate infinite neogenetic tissue. That is, before cultivation, the cell construct 6 is combination of all or a part of a cell, a culture fluid, a hydro gel and a gel scaffold. After cultivation, the cell construct 6 is converted into combination of all or a part of a cell, a culture fluid, a hydro gel, a gel scaffold, an extracellular matrix and other products of a cell.

If such culture is injected into a damaged or deficit part in vivo, original tissue is regenerated at the injected part in vivo, and the injected culture can amalgamate with tissue therearound.

The cell construct 6 is, as shown in FIG. 19, entered into the tube 202 of a semi-permeable membrane. In this case, the cell construct 6 is what a cell is disseminated on a finite cell scaffold 205. Each opening at the edges of the tube 202 is sealed by the stopper 206.

The single or a plurality of the cell construct 6 are arranged and attached to the culture bed 36, and repeatedly curved. From this, a cell is propagated, and an extracellular matrix and so on are generated to generate infinite neogenetic tissue. That is, before cultivation, the cell construct 6 is composed of a cell, a cell scaffold such as a collagen sponge and a gel scaffold. After cultivation, the cell construct 6 is generated into neogenetic tissue composed of a cell, a cell scaffold, an extracellular matrix and other products of a cell.

When a semi-permeable membrane is taken off, inside neogenetic tissue is taken out, and the neogenetic tissue is transplanted to a damaged or a deficit part of a human body by suture, adhesive, etc., an original tissue is regenerated at a transplanted part and, the neogenetic tissue can be amalgamated with tissue therearound.

Third Embodiment

Figure 20:
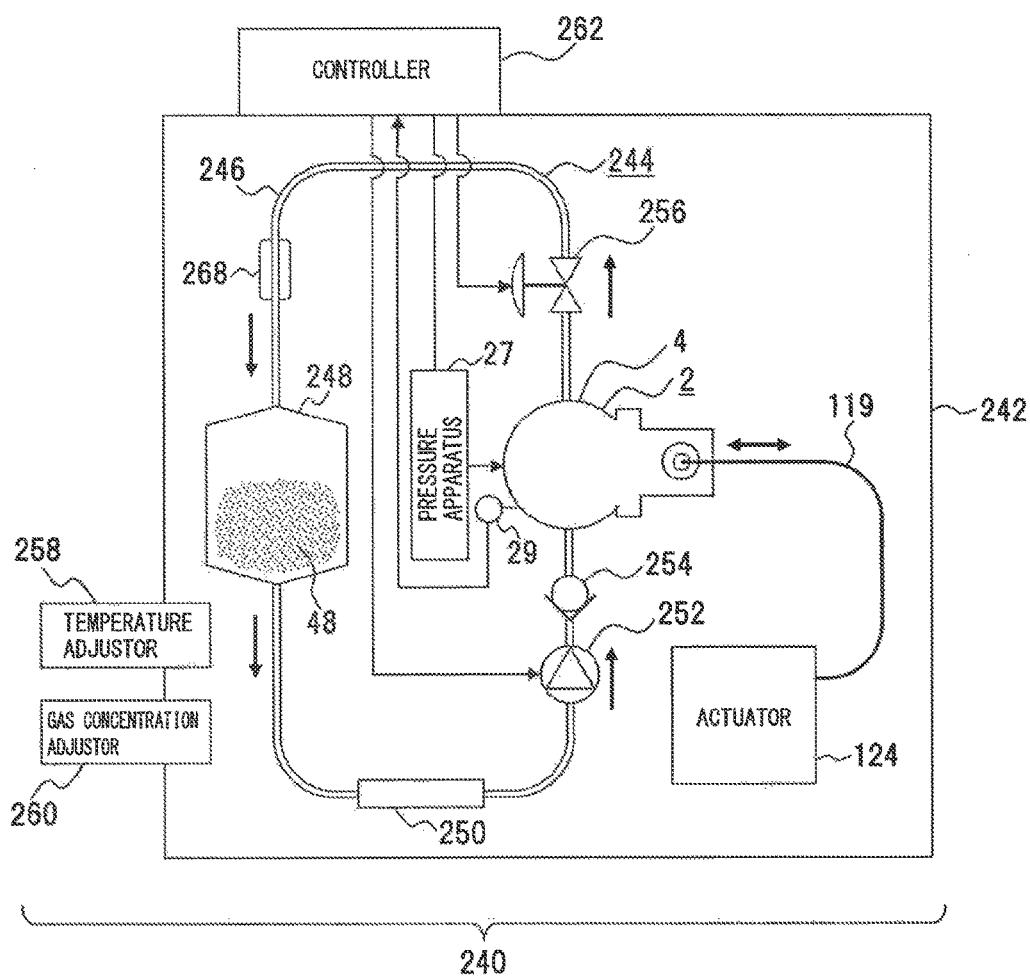
FIG. 20 is a view showing a cultivation system according to a third embodiment.
Figure 21:
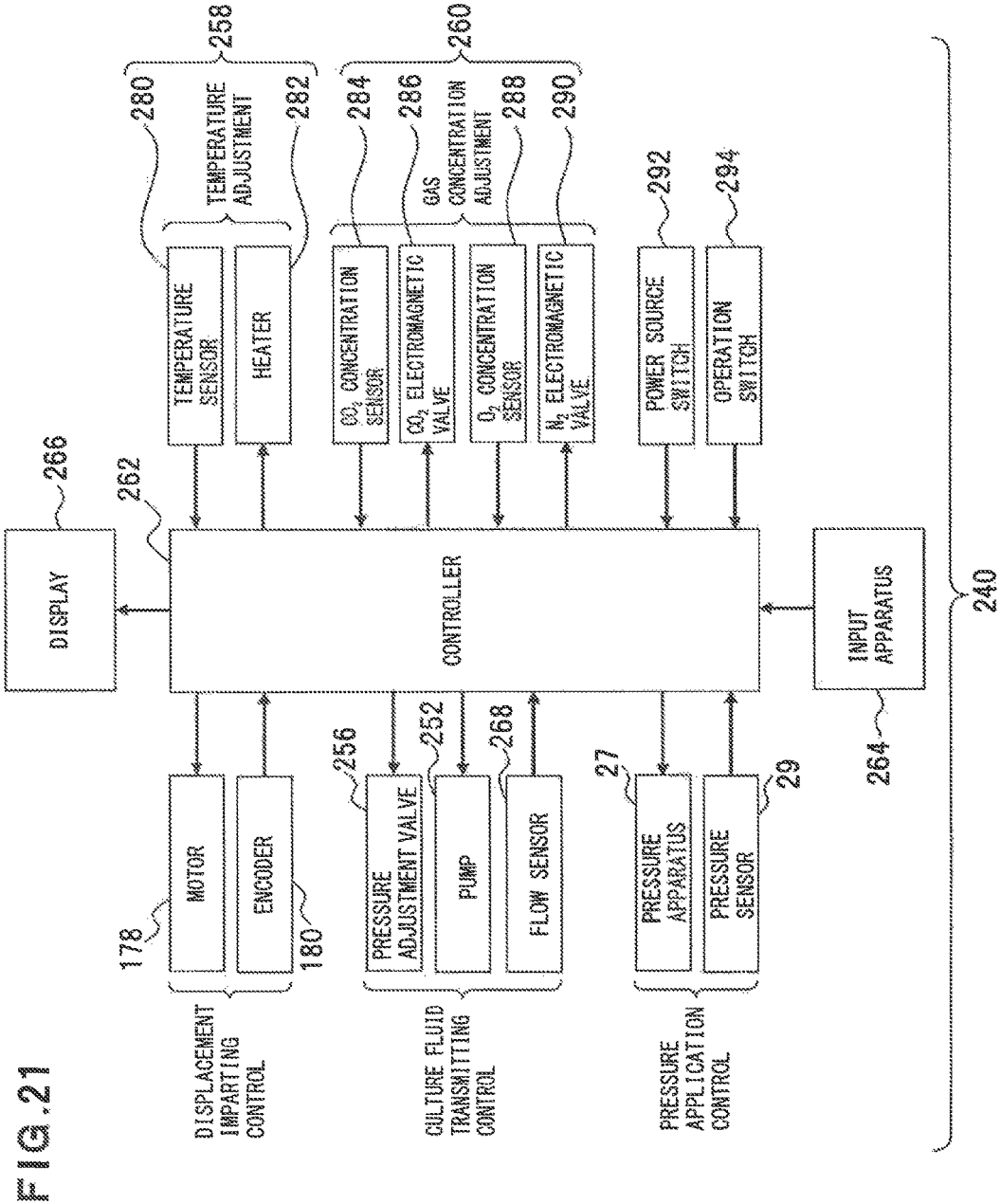
FIG. 21 is a block diagram showing a control system of a cultivation system.
Figure 22:
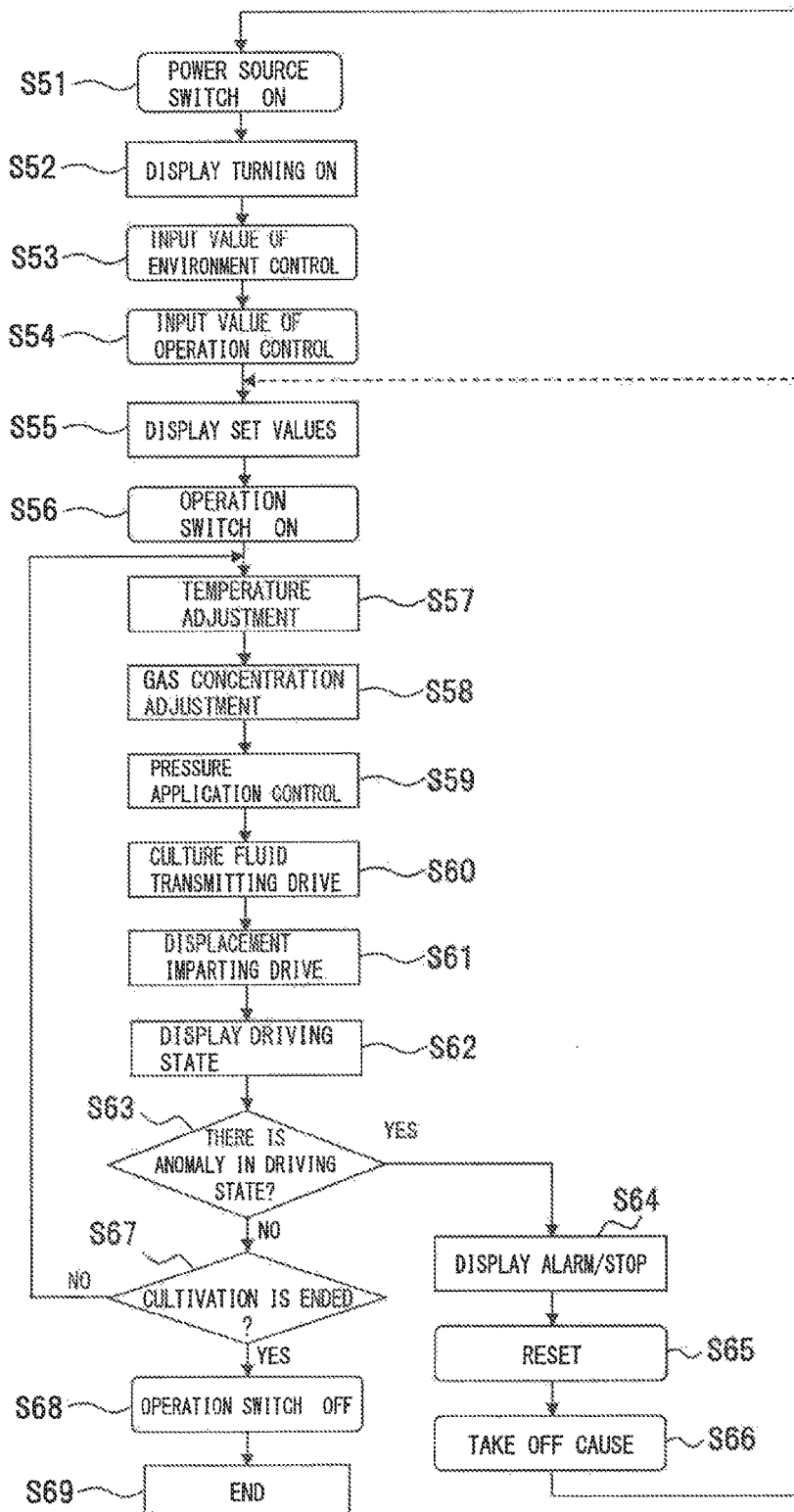
FIG. 22 is a flowchart showing processing procedure of a cultivation system.

A third embodiment the present invention will be described with referring to FIGS. 20-22. FIG. 20 depicts a cultivation system according to a third embodiment, FIG. 21 depicts a structural example of a control unit and FIG. 22 is a flowchart showing processing procedure of a cultivation operation.

In a cultivation system 240, for circulating a culture fluid 48 and supplying the fresh culture fluid 48 at any time, a culture circuit 244 including an incubator unit 4 of a culture unit 2 is provided in a culture room 242. The culture circuit 244 composes a circulation path that connects a culture fluid tank 248, a gas exchanger 250, a pump 252, a check valve 254, the incubator unit 4 and a pressure adjusting valve 256 via a circulation tube 246. In the culture circuit 244, the culture fluid 48 can be circulated optionally. As one aspect of control of the circulation, for example, if circulation of the culture fluid 48 is stopped or inhibited, the culture circuit 244 may be shut. The above pump 252 is composed of a piston pump, a syringe pump and a peristaltic pump, etc. With the circulation tube 246, for example, a flow sensor 268 that detects a flow of the culture fluid 48 by a method such as counting drops of the culture fluid 48 is provided.

In the culture room 242, a temperature adjustor 258, a gas concentration adjustor 260 and a controller 262 are provided. In the culture room 242, temperature necessary for cultivation is set by the temperature adjustor 258, constant gas concentration is maintained by the gas concentration adjustor 260, and circulation of the culture fluid 48 and pressure in the incubator unit 4 are controlled by the controller 262.

To the incubator unit 4, bending stress is imparted from an actuator 124 via a cable 119. In this case, the actuator 124 is provided in the culture room 242. The actuator 124 may be provided outside the culture room 242.

Motion of the actuator 124 may be controlled along with pressurized circulation of the culture fluid 48, or controlled independently. In this case, pressure application to the culture fluid 48 and bending stress by the actuator 124 are imparted to the cell construct 6.

For the cell construct 6, to control imparting of bending displacement, circulation of the culture fluid 48 and pressure in the incubator unit 4 together, as shown in FIG. 21, a control system may be configured. In the controller 262, rotational speed of a motor 178 and the amount of circulation of the culture fluid 48 are set from an input apparatus 264, and the motor 178 and the pump 252 are driven. The controller 262 is configured by a computer including a CPU (Central Processing Unit), a ROM (Read-Only Memory) and a RAM (Random-Access Memory).

The motor 178, an encoder 180 and the controller 262 execute displacement imparting control. Rotation of the motor 178 is detected by the encoder 180, and detected information is inputted to the controller 262.

The pressure adjusting valve 256, the pump 252, the flow sensor 268 and the controller 262 execute culture fluid transmission control. In this culture fluid transmission control, if rotational speed of the pump 252 rises, the amount of a flow of the culture fluid 48 increases. Pressure by fluid transmission can be adjusted by the pressure adjusting valve 256. A flow of the culture fluid 48 is, for example, detected by the flow sensor 268 with using a method such as counting drops of the culture fluid 48, and detected information is used in control information such as pump control.

The pressure apparatus 27, the pressure sensor 29 and the controller 262 execute pressure application control. The pressure sensor 29 detects pressure, and by detected information, pressure application control is executed.

A temperature sensor 280 and a heater 282 that constitute the temperature adjuster 258, and the controller 262 execute temperature adjustment control. Based on detected information of the temperature sensor 280, heat generation temperature of the heater 282 is controlled. A $CO_2$ concentration censor 284, a $CO_2$ electromagnetic valve 286, an $O_2$ concentration sensor 288, and an $N_2$ electromagnetic valve 290 that constitute the gas concentration adjuster 260, and the controller 262 execute gas concentration control. Based on detected information of the $CO_2$ concentration sensor 284, a degree of opening of the $CO_2$ electromagnetic valve 286 is controlled. Based on detected information of the $O_2$ concentration sensor 288, a degree of opening of the $N_2$ electromagnetic valve 290 is controlled. This control of temperature adjustment and gas concentration execute environment control in the culture room 242. That is, according to gas concentration atmosphere in the culture room 242, in the gas exchanger 250, gas is exchanged between the culture fluid 48 and the culture room 242.

In such cultivation system 240, as shown in FIG. 22, turning on a power source switch 292 (step S51) lights a display 266 (step S52). Thus, after input of a value of environment control (step S53) and input of a value of control operation (step S54), setting values are displayed on the display 266 (step S55). Here, an operation switch 294 is turned on (step S56).

If the cultivation system 240 is in an operation state, temperature adjustment (step S57), gas concentration adjustment (step S58), pressure application control (step S59), culture fluid transmission drive (step S60) and displacement imparting drive (step S61) are executed, and a driving state is displayed on the display 266 (step S62).

A driving state necessary for displacement imparting is monitored (step S63). If there is anomaly, after an alarm is displayed, drive is stopped (step S64), the cultivation system 240 is reset (step S65), a cause of anomaly is taken off (step S66), steps S51-S63 are operated again, and cultivation is ended (step S67). After ending cultivation, the operation switch 294 is turned off (step S68), and a cultivation process is ended (step S69).

Fourth Embodiment

Figure 23:
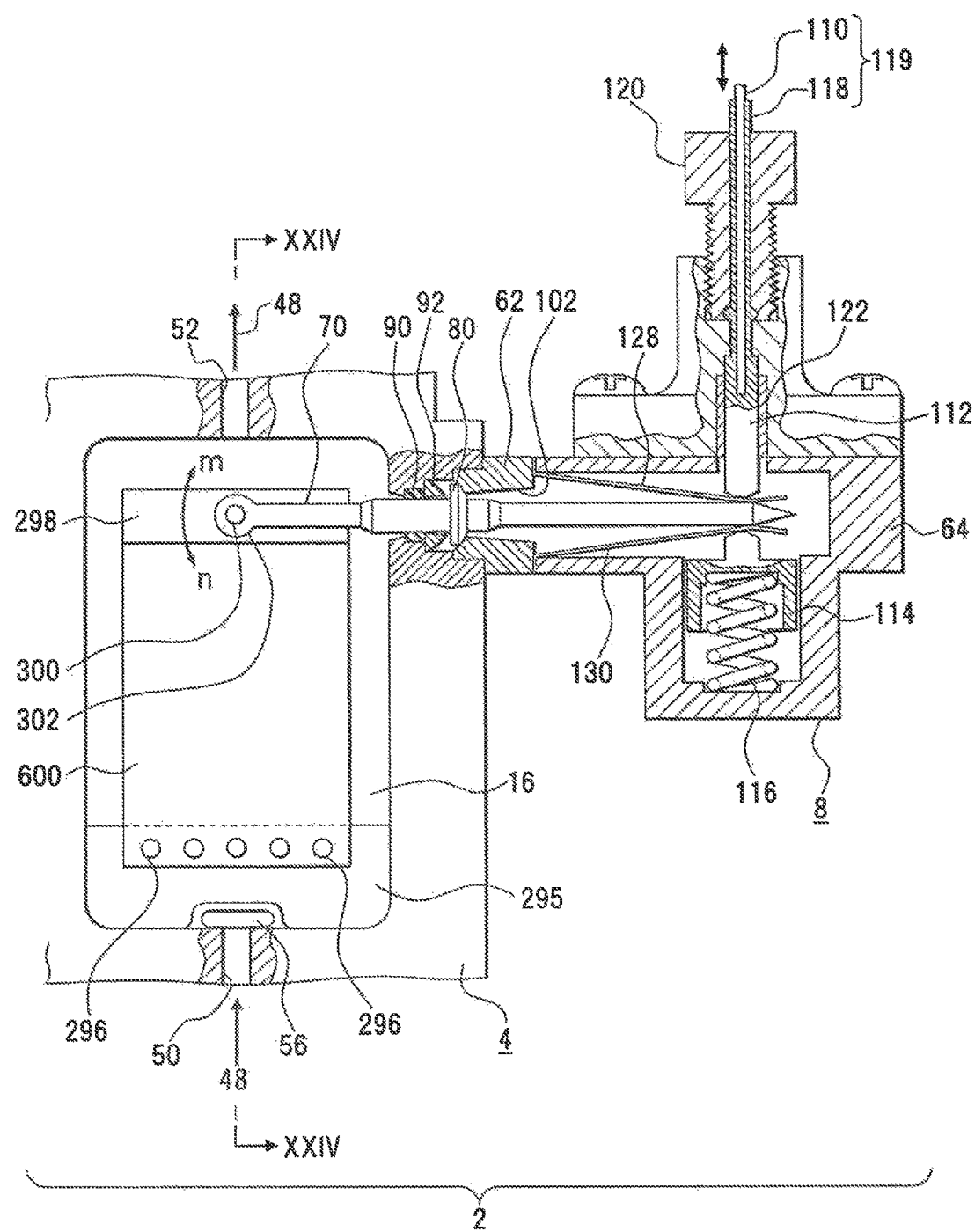
FIG. 23 is a view showing a culture unit of a cultivation apparatus according to a fourth embodiment.
Figure 24:
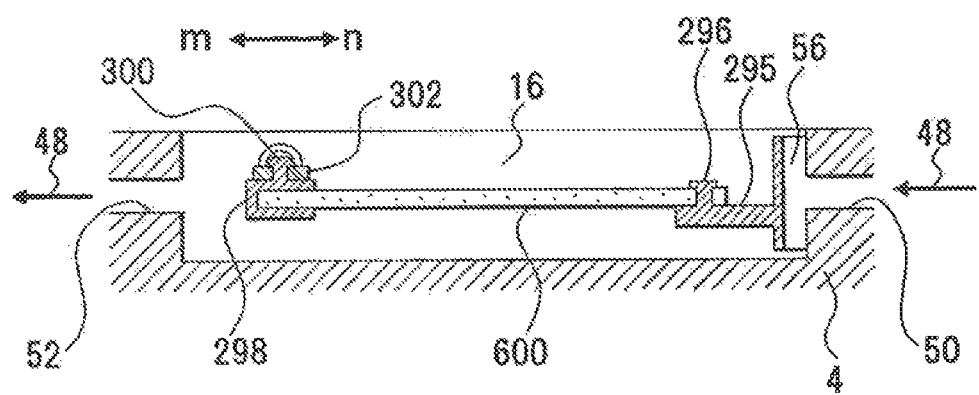
FIG. 24 is a sectional view of FIG. 23 along an XXIV-XXIV line.

A fourth embodiment of the present invention will be described with referring to FIGS. 23 and 24. FIG. 23 depicts a culture unit according to a fourth embodiment, and FIG. 24 depicts a section of FIG. 23 along an XXIV-XXIV line. In FIGS. 23 and 24, the same parts as those in FIGS. 1-8 are denoted by the same reference numerals.

In the first to third embodiments, a process of imparting bending displacement to the cell construct 6 is described. The present invention can apply to an extension and contracting process of a cell construct 600. A desired displacement can be imparted to the cell construct 600 without generating change of inner pressure in a culture space 16 of an incubator unit 4 by movement of a lever 70.

In the incubator unit 4 of this embodiment, the rectangular culture space 16 is formed. One end of the cell construct 600 is attached to a protrusion 296 that protrudes from a shelf 295 of the culture space 16, and a tip of the lever 70 is rotatably fixed to a holding frame 298 that is attached to the other end of the cell construct 600. In this embodiment, a fixing pin 300 is protruded over the holding frame 298. An engaging ring 302 that is formed at the tip of the lever 70 is movably engaged with this fixing pin 300.

From such structure, if the lever 70 is rotated in a circular arc by stress imparted from an actuator 124 (FIGS. 8 and 9) to a driving unit 8 via a wire 110, the cell construct 6 is extended and contracted in directions of arrows m and n in accordance with rotation in circulate arc, and stimulation, imparting of tension and cancellation thereof necessary for cultivation can be repeatedly executed.

In this case, a culture fluid 48 is poured into the culture space 16 from an inlet port 50, poured out from an outlet port 52, thus, the fresh culture fluid 48 can be supplied to the cell construct 600.

Features Extracted from the Embodiments

Concerning features extracted from the embodiments described above, features except matters described in claims are as follows. Listed features do not limit the present invention.

(1) The above cultivation apparatus, wherein the bed and the lever are disposed in parallel or perpendicularly.

(2) The above cultivation apparatus, wherein the incubator unit is sealed structure.

(3) The above cultivation apparatus, wherein an edge of the lever has an action unit.

(4) The above cultivation apparatus, wherein the bed holds the culture, curves by receiving pressure from the lever and restores a state before applying pressure by cancelling the pressure application.

(5) The above cultivation apparatus, wherein the bed comprises a holding unit, at an edge of the bed, that the incubator unit holds, and a receiving unit, at a middle part of the bed, that receives action from the lever.

(6) The above cultivation apparatus, wherein the lever comprises a flange that has circular arc face in the vicinity of the fulcrum, a joint part having a circular arc face correspondingly to the flange is included in the incubator unit, and the circular arc face of the flange and the circular arc face of the joint part are slideably contacted.

(7) The above cultivation apparatus, wherein in the joint part, when the lever is rotated, the center of rotation of the lever corresponds with a center of a sealing part of the lever.

(8) The above cultivation apparatus, wherein a driving unit that imparts driving force to a rear end of the lever extracted from the incubator unit is provided at a side of the incubator unit.

(9) The above cultivation apparatus, wherein the driving unit is disposed detachably and attachably in the incubator unit.

(10) The above cultivation apparatus, comprising a control part that controls the pressure application imparted from the driving unit to the lever periodically and consequently, and/or controls application pressure velocity.

(11) The above cultivation apparatus, wherein to the incubator unit, a culture fluid is supplied from a supplying port and exhausted from an exhausting port.

(12) A cultivation apparatus comprising a diaphragm in an incubator unit, wherein pressure can be applied into the incubator unit via the diaphragm.

(13) The above cultivation apparatus, wherein the driving unit comprises a housing unit that is disposed at a side of the incubator unit, a first slider that is slideably held in the housing, slides by driving force applied from an outside, and generates circular arc movement to the lever, and a second slider that is slideably held in the housing, and acts restoring force on the lever in an opposite direction from the slider.

(14) The above cultivation apparatus, wherein the housing comprises an inserting port where the lever is inserted, and a guide part that guides an end of the lever inserted from the inserting port between the first slider and the second slider.

Result of Experiment

A result of an experiment using the above cultivation apparatus and the cultivation system will be described with referring to FIGS. 25 to 29.

Figure 25:
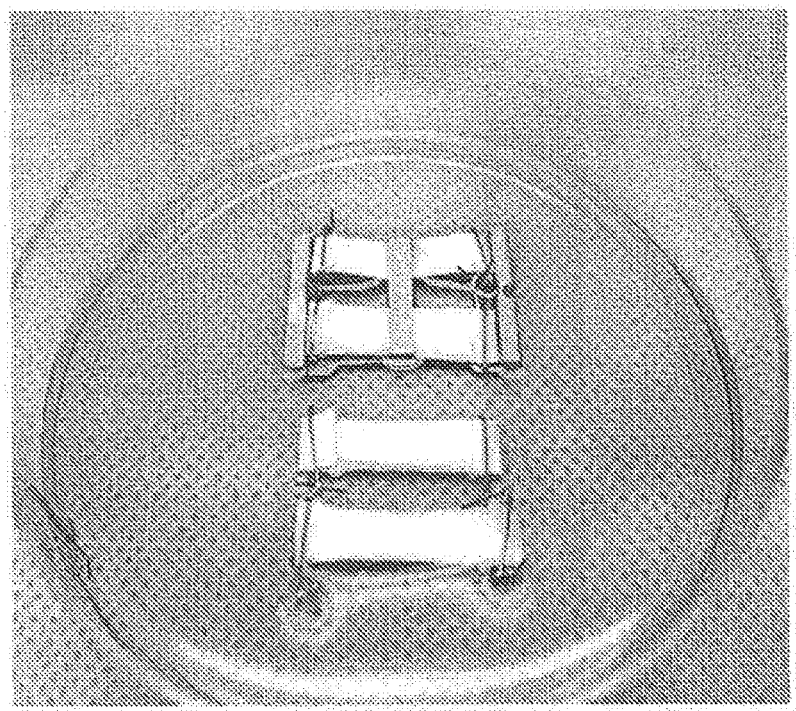
FIG. 25 is a view showing an experimental example.
Figure 26:
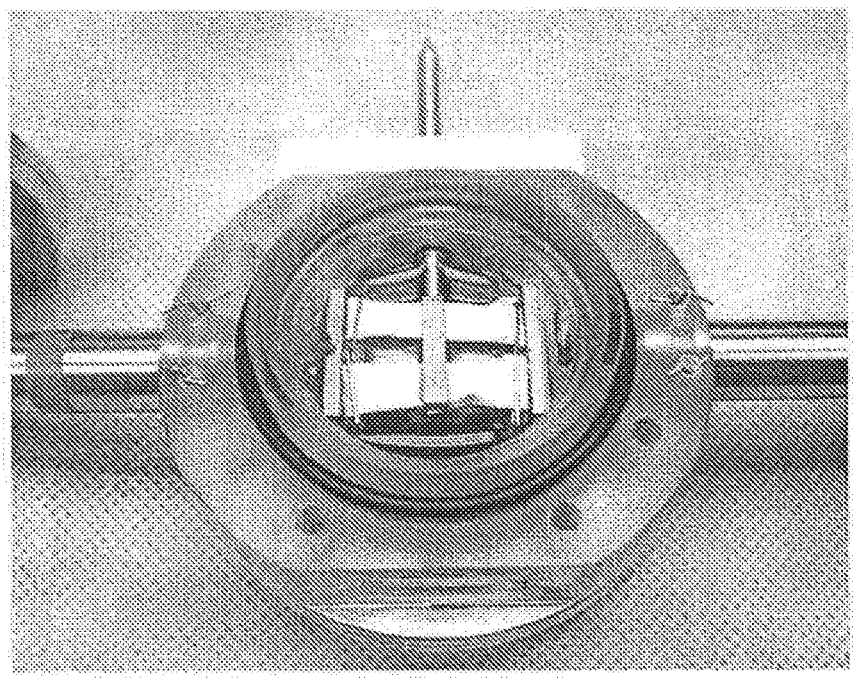
FIG. 26 is a view showing an experimental example.

FIG. 25 shows a cell construct. This cell construct is composed of entering a cell suspended in a culture fluid into a tube of a semi-permeable membrane. As shown in FIG. 26, the cell construct is fixed to a culture bed, and is accommodated in an incubator unit (chamber). In this case, a driving unit is separated from the incubator unit.

Pressure from an actuator acts on a culture unit, and bending motion is imparted to the cell construct. The actuator is disposed outside a culture room. A cable was penetrated through a door of the culture room to be connected to the driving unit. An operation state of the actuator could be confirmed by a display.

The actuator converts a rotational movement of a motor to linear movement by a crank. By selection of the length of a crank arm, width of back and forth of a wire could be adjusted, and in accordance with this selection, a size of bending imparted to the cell construct can be adjusted.

In this experiment, pressure application operation is limited to bending motion, atmospheric pressure is maintained and the culture fluid is circulated. Pressure and bending motion by the actuator are imparted individually, irrelevantly and solely. In the experiment, for example, it can be considered that pressure equal to or over 0.5 (MPa) is imparted.

Figure 27:
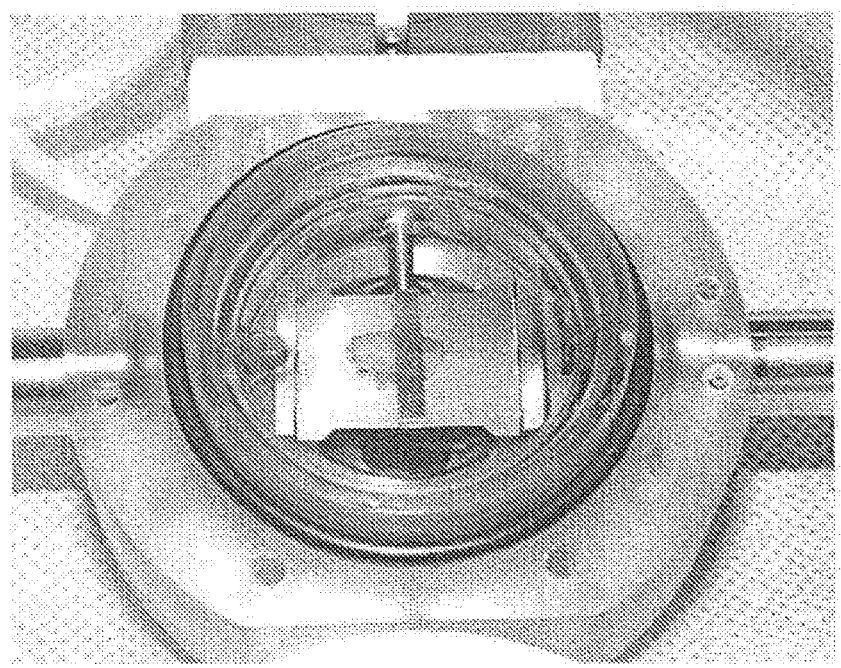
FIG. 27 is a view showing an experimental example.
Figure 28:
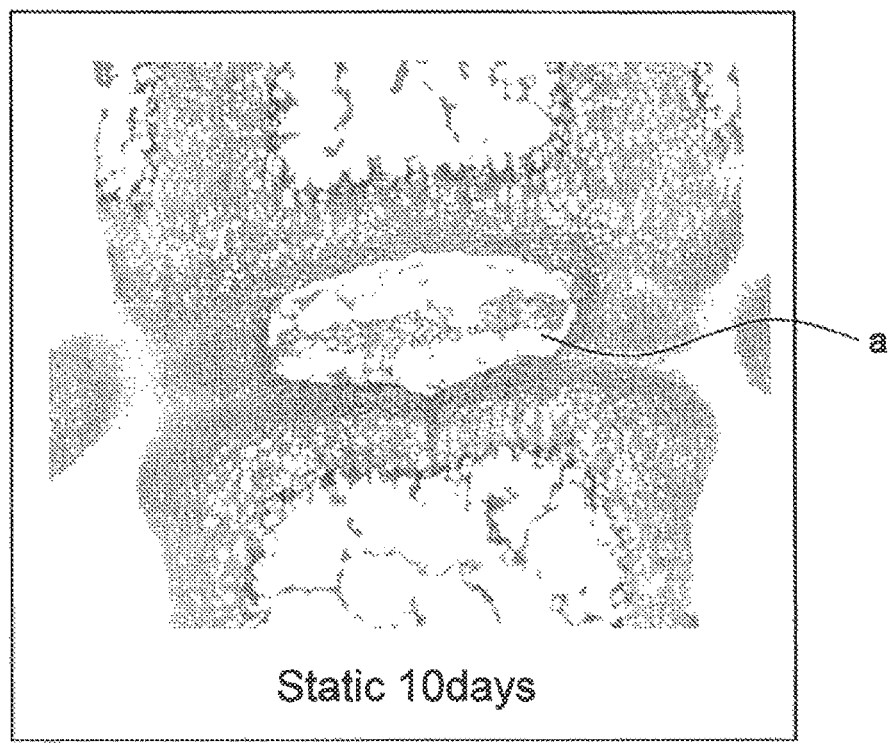
FIG. 28 is a view showing an experimental example.
Figure 29:
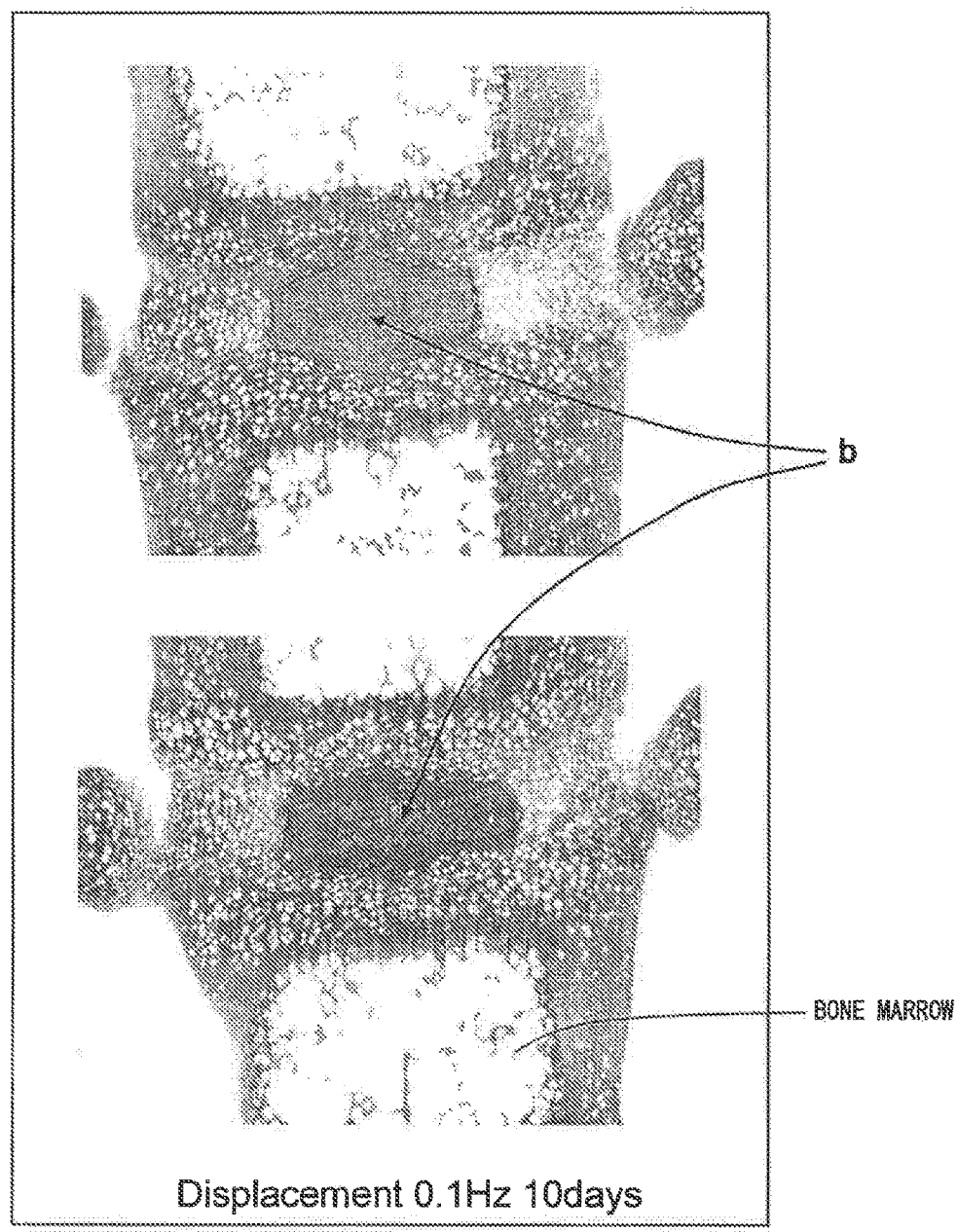
FIG. 29 is a view showing an experimental example.

FIGS. 27 to 29 show an experiment of vertebrae organ cultivation of a two days old mouse. In the experiment, a vertebra taken out from the two days old mouse is disposed on the culture bed (FIG. 27) and bending motion of 0.1 (Hz) frequencies is imparted to be cultivated for ten days. In this experiment, no pressure is applied.

As a comparison example, static cultivation is executed. FIGS. 28 and 29 show static cultivation for ten days. After ten days, a section of an organ is toluidine blue-stained, and condition of a cell existence is observed. In Figs., a stained part can not be expressed. A part where brightness falls down (a stained part) shows existence of a living cell. In the static cultivation, cell density inside discs does not rise, and displacement of matrixes can be seen (a of FIG. 28).

On the contrary, in vertebrae where bending motion and displacement are imparted, growth of cells and store of neogenetic matrixes inside discs can be seen. (b of FIG. 29).

From the result of the experiment, in the cultivation of imparting bending motion, growth of cells and store of neogenetic matrixes can be seen as prepared with the static cultivation. Thus, it can be guessed that the bending motion gives stimulation to the cell construct, and makes substance migration promote.

While the present invention has been described with the preferred embodiments, the description is not intended to limit the present invention.

The present invention relates to a cultivation apparatus for a culture including a cell and/or tissue. A cultivation apparatus for a cell and/or tissue proper to a region of a human body, etc. is provided. By imparting bending motion to a cell construct, tissue cultivation of vertebra, etc. can be executed efficiently. So, the present invention is useful.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiment(s) of the present invention(s) has(have) been described in detail, it should be understood that the various changes, substitutions, and alterations could be made hereto without departing from the spirit and scope of the invention.

The invention claimed is:

1. A cultivation apparatus for a culture including a cell and/or tissue, comprising:
   an incubator unit that accommodates the culture, one end of the culture in a longitudinal direction being fixed to the incubator unit; and
   a lever that penetrates from an inside of the incubator unit to an outside thereof, the lever having an action unit to which another end of the culture in the longitudinal direction is fixed, the action unit being disposed in the incubation unit, the lever moving in circular arc around a fulcrum as a center to allow the action unit to move back and forth in the longitudinal direction of the culture, the fulcrum being set at a wall of the incubator unit or in the vicinity thereof,
   wherein movement of the lever in circular arc makes the action unit in the incubator unit move back and forth, and
   the culture is extended and contracts in the longitudinal direction thereof in response to back and forth movement of the action unit of the lever.

2. A cultivation apparatus according to claim 1, wherein the incubator unit is sealed structure.

3. A cultivation apparatus according to claim 1, wherein the lever comprises a flange having a circular arc face in the vicinity of the fulcrum, a joint part having a circular arc face correspondingly to the flange is included in the incubator unit, and the circular arc face of the flange and the circular arc face of the joint part are slideably contacted.

4. A cultivation apparatus according to claim 3, wherein in the joint part, when the lever is rotated, the center of rotation of the lever corresponds with a center of a sealing part of the lever.

5. A cultivation apparatus according to claim 1, wherein a driving unit that imparts driving force to a rear end of the lever extracted from the incubator unit is provided at a side of the incubator unit.

6. A cultivation apparatus according to claim 5, wherein the driving unit is disposed detachably and attachably to the incubator unit.

7. A cultivation apparatus according to claim 5, further comprising:
   a control part that controls the driving force imparted from the driving unit to the lever periodically and consequently, and/or controls application pressure velocity.

8. A cultivation apparatus according to claim 1, wherein a culture fluid is supplied to the incubator unit from a supplying port and exhausted from an exhausting port.

9. A cultivation apparatus according to claim 1, further comprising:
   a diaphragm that is disposed over a window, the window being formed in the incubator unit, wherein pressure can be applied into the incubator unit via the diaphragm.

10. A cultivation apparatus according to claim 5, wherein the driving unit comprises a housing unit that is disposed at a side of the incubator unit;
    a first slider that is slideably attached to the housing, slides by driving force applied from an outside, and generates circular arc movement to the lever; and
    a second slider that is slideably attached to the housing, and acts restoring force on the lever in an opposite direction from the slider.

11. A cultivation apparatus according to claim 10, wherein the housing comprises an inserting opening where the lever is inserted; and
    a guide part that guides an end of the lever, which is inserted through the inserting opening, to a position between the first slider and the second slider.

12. A cultivation apparatus for a culture including a cell and/or tissue, comprising:
    a holding frame that is attached to one end of the culture in a longitudinal direction;
    an incubator unit that accommodates the culture, another end of the culture in the longitudinal direction being fixed to the incubator unit; and
    a lever that penetrates from an inside of the incubator unit to an outside thereof, the lever having an action unit that is fixed to the holding frame, which is attached to said one end of the culture, the action unit being disposed in the incubator unit, the lever moving in circular arc around a fulcrum as a center to allow the action unit to move back and forth in the longitudinal direction of the culture, the fulcrum being set at a wall of the incubator unit or in the vicinity thereof,
    wherein movement of the lever in circular arc makes the action unit in the incubator unit move back and forth, and
    the culture is extended and contracts in the longitudinal direction thereof in response to back and forth movement of the action unit of the lever.

* * * * *